(12) United States Patent
Chen et al.

(10) Patent No.: US 7,435,739 B2
(45) Date of Patent: Oct. 14, 2008

(54) SUBSTITUTED PYRROLOPYRIMIDINES USEFUL IN THE TREATMENT OF CANCER

(76) Inventors: Jinshan Chen, 42 Ben Merrill Rd., Clinton, CT (US) 06413; Matthew A. Marx, 160 Niles Hill Rd., Waterford, CT (US) 06385; Susan D. LaGreca, 1 Long Acre La., Old Lyme, CT (US) 06371; Matthew D. Wessel, 12 Greystone Ct., Groton, CT (US) 06339

(*) Notice: Subject to any disclaimer, the term of this patent is extended or adjusted under 35 U.S.C. 154(b) by 407 days.

(21) Appl. No.: 10/989,842

(22) Filed: Nov. 16, 2004

(65) Prior Publication Data

US 2005/0130994 A1 Jun. 16, 2005

Related U.S. Application Data

(60) Provisional application No. 60/523,206, filed on Nov. 17, 2003.

(51) Int. Cl.
*C07D 487/04* (2006.01)
*A61K 31/519* (2006.01)
*A61K 31/664* (2006.01)
*C07F 9/24* (2006.01)
*A61P 35/04* (2006.01)

(52) U.S. Cl. .................... 514/265.1; 544/280; 544/243; 514/81

(58) Field of Classification Search ................ 544/280, 544/243; 514/265.1, 81
See application file for complete search history.

(56) References Cited

U.S. PATENT DOCUMENTS

2003/0199525 A1  10/2003  Hirst et al. ............... 514/260.1

FOREIGN PATENT DOCUMENTS

| WO | 9823613 | 6/1998 |
|---|---|---|
| WO | 0017202 | 3/2000 |
| WO | 03000695 | 1/2003 |
| WO | 2004013141 | 2/2004 |
| WO | 2004056830 | 7/2004 |

*Primary Examiner*—Brenda Coleman
*Assistant Examiner*—Susanna Moore
(74) *Attorney, Agent, or Firm*—Bryan C. Zielinski; Galina M. Yakovleva

(57) ABSTRACT

The invention relates to compounds of the formula 1

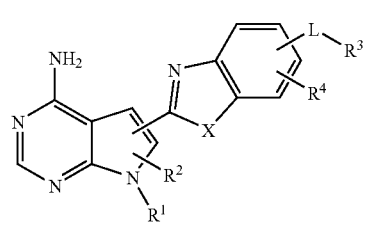

or a pharmaceutically acceptable salt, prodrug or hydrates thereof, wherein X, L, $R^1$, $R^2$, $R^3$ and $R^4$ are as defined herein. The invention also relates to pharmaceutical compositions containing the compounds of formula 1 and to methods of treating hyperproliferative disorders in a mammal by administering the compounds of formula 1.

34 Claims, No Drawings

SUBSTITUTED PYRROLOPYRIMIDINES USEFUL IN THE TREATMENT OF CANCER

This application claims the benefit of provisional application Ser. No. 60/523,206, filed Nov. 17, 2003. The entire disclosure of parent application filed is fully incorporated herein by reference thereto.

BACKGROUND OF THE INVENTION

This invention relates to novel pyrrolopyrimidine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

It is known that a cell may become cancerous by virtue of the transformation of a portion of its DNA into an oncogene (i.e. a gene that upon activation leads to the formation of malignant tumor cells). Many oncogenes encode proteins, which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate specific tyrosine residue in proteins and hence to influence cell proliferation. The foregoing tyrosine kinases may be classified as growth factor receptor (e.g. TIE-2,TrkA, EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or overexpressed in many human cancers such as brain, lung, squamous cell, bladder, gastric, breast, head and neck, esophageal, gynecological and thyroid cancers. Thus, it is believed that inhibitors of receptor tyrosine kinases, such as the compounds of the present invention, are useful as selective inhibitors of the growth of mammalian cancer cells.

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli.

The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovascularization. By adenoviral infection, the in vivo production of mg/ml levels ExTek in rodents may be achieved for 7-10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, therefore, useful in treating such disorders, and in other situations of inappropriate neovascularization. The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. Agents, such as the compounds of the present invention, that are capable of binding to or modulating the Tie-2 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

Patent publications referring to pyrrolopyrimidines as protein kinase inhibitors include the following: WO 01/72751 (published Oct. 4, 2001), WO 00/17203 and WO 00/17202 (both published Mar. 30, 2000), U.S. Pat. No. 6,001,839 (granted Dec. 14, 1999), and U.S. Pat. No. 6,051,577 (granted Apr. 18, 2000). WO 01/72778 (published Oct. 4, 2001) refers to polypeptides comprising the catalytic domain of a Tie-2 protein. U.S. Provisional Application Ser. No. 60/434,568, filed Dec. 19, 2003, refers to pyrrolopyrimidine derivatives useful in the treatment of hyperproliferative diseases, such as cancers.

Compounds that are useful in the treatment of hyperproliferative diseases are referred to the following patent publications: International patent application publication numbers WO 97/49688 (published Dec. 31, 1997), WO 98/23613 (published Jun. 4, 1998), WO 96/40142 (published Dec. 19, 1996), WO 97/13771 (published Apr. 17, 1997), and WO 95/23141 (published Aug. 31, 1995); European patent publication numbers EP 0837063 (published Apr. 22, 1998), and EP 0907649 (published Apr. 14, 1999); and U.S. Pat. No. 5,747,498 (granted May 5, 1998), and U.S. Pat. No. 6,492,383 (granted Dec. 10, 2002).

SUMMARY OF THE INVENTION

The present invention provides compounds of the formula 1

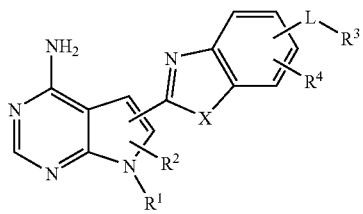

or a pharmaceutically acceptable salt, prodrug, solvate or hydrate thereof, wherein:

X is HN, $(C_1\text{-}C_6)$alkyl-N, $(C_3\text{-}C_8)$cycloalkyl-N, O or S;

L is —$(CH_2)_p$—, wherein p is an integer from 0 to 5; —O—; —S—; —S(O)—; —S(O)$_2$; —N(R)—; —N(C(O)OR)—; —N(C(O)R)—; —N(S(O)$_2$R)—; —CH$_2$O—; —CH$_2$S—; —CH$_2$N(R)—; —C(=NR)—; —CH$_2$N(C(O)R)—; —CH$_2$N(C(O)OR)—; —CH$_2$N(S(O)$_2$R)—; —CH(NHR)—; —CH(NHC(O)R)—; —CH(NHS(O)$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; —OC(O)N(R)—; —N(R)C(O)N(R)—; —N(R)C(O)O—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —S(O)N(C(O)R)—; —S(O)$_2$N(C(O)R)—; —N(R)S(O)N(R)—; —N(R)S(O)$_2$N(R)—; —C(O)O—; —N(R)P(OR$^5$)O—; —N(R)P(OR$^5$)—; —N(R)P(O)(OR$^5$)O—; —N(R)P(O)(OR$^5$)—; —N(C(O)R)P(OR$^5$)O—; —N(C(O)R)P(OR$^5$)—; —N(C(O)R)P(O)(OR$^5$)O—; —N(C(O)R)P(OR$^5$)—, —CH(R)S(O)—; —CH(R)S(O)$_2$—; —CH(R)N(C(O)OR$^5$)—; —CH(R)N(C(O)R)—; —CH(R)N(SO$_2$R)—; —CH(R)O—; —CH(R)S—; —CH(R)N(R)—; —CH(R)N(C(O)R)—; —CH(R)N(C(O)OR)—; —CH(R)N(SO$_2$R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; —CH(R)N(R)S(O)$_2$—; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; —CH(R)N(R)S(O)O—; —CH(R)N(R)S(O)$_2$O—; —CH(R)N(R)S(O)C(O)—; —CH(R)N(R)S(O)$_2$C(O)—; —CH(R)S(O)N(C(O)R)—; —CH(R)S(O)$_2$N(C(O)R)—; —CH(R)N(R)S(O)N(R)—; —CH(R)N(R)S(O)$_2$N(R)—; —CH(R)C(O)O—; —CH(R)N(R)P(OR$^5$)O—; —CH(R)N(R)P(OR$^5$)—; —CH(R)N(R)P(O)(OR$^5$)O—; —CH(R)N(R)P(O)(OR$^5$)—; —CH(R)N(C(O)R)P(OR$^5$)O—; —CH(R)N(C(O)R)P(OR$^5$)—; —CH(R)N(C(O)R)P(O)(OR$^5$)O— or —CH(R)N(C(O)R)P(OR$^5$)—; wherein each R is independently selected from the group consisting of H, $(C_1\text{-}C_6)$alkylcarbonyl, $(C_1\text{-}C_6)$alkyl, $(C_6\text{-}C_{10})$aryl and $(C_1\text{-}C_{10})$heteroaryl; wherein each of the aforesaid $(C_1\text{-}C_6)$alkylcarbonyl, $(C_1\text{-}C_6)$alkyl, $(C_6\text{-}C_{10})$aryl, and $(C_1\text{-}C_{10})$heteroaryl groups is independently optionally substituted with 1-3 substituents independently selected from halogen, $(C_1\text{-}C_6)$alkyl and $(C_1\text{-}C_6)$alkoxy;

$R^1$ is H, $(C_1\text{-}C_6)$alkyl, $(C_3\text{-}C_8)$cycloalkyl, $(C_6\text{-}C_{10})$aryl, $(C_1\text{-}C_{10})$heteroaryl, or $(C_1\text{-}C_{10})$heterocycloalkyl, wherein each of the aforesaid $(C_1\text{-}C_6)$alkyl, $(C_3\text{-}C_8)$cycloalkyl, $(C_6\text{-}C_{10})$aryl, $(C_1\text{-}C_{10})$heteroaryl, and $(C_1\text{-}C_{10})$heterocycloalkyl groups is optionally independently substituted with 1 to 5 $(C_1\text{-}C_6)$alkyl groups;

$R^2$ is H, halo, $(C_1\text{-}C_6)$alkyl, $(C_3\text{-}C_8)$cycloalkyl, $(C_6\text{-}C_{10})$aryl, $(C_1\text{-}C_{10})$heteroaryl, $(C_3\text{-}C_8)$heterocycloalkyl, —$(CR^{10}R^{11})_n NR^6 R^7$ or —$(CR^{10}R^{11})_n C(O)NR^6 R^7$; wherein n is an integer from 0-3; and each of the aforesaid $(C_1\text{-}C_6)$alkyl, $(C_3\text{-}C_8)$cycloalkyl, $(C_6\text{-}C_{10})$aryl, $(C_1\text{-}C_{10})$heteroaryl, and $(C_3\text{-}C_8)$heterocycloalkyl groups is optionally independently substituted with 1 to 5 $R^8$ substituents;

$R^3$ is H, $(C_1\text{-}C_6)$alkyl, $(C_3\text{-}C_8)$cycloalkyl, —$(CR^{10}R^{11})_t (C_6\text{-}C_{10})$aryl, —$(CR^{10}R^{11})_t (C_1\text{-}C_{10})$heteroaryl, or $(C_3\text{-}C_6)$heterocycloalkyl; wherein t is independently an integer from 0 to 6; and each of the aforesaid $(C_1\text{-}C_6)$alkyl, $(C_3\text{-}C_8)$cycloalkyl, —$(CR^{10}R^{11})_t(C_6\text{-}C_{10})$aryl, —$(CR^{10}R^{11})_t(C_1\text{-}C_{10})$heteroaryl, and $(C_3\text{-}C_8)$heterocycloalkyl groups is optionally independently substituted with 1 to 5 $R^{12}$ groups;

$R^4$ is H, halo, $(C_1\text{-}C_6)$alkyl, $(C_3\text{-}C_6)$cycloalkyl, $(C_1\text{-}C_6)$alkoxy, or $(C_3\text{-}C_6)$cycloalkoxy;

each $R^5$ is independently H, $(C_1\text{-}C_6)$alkylcarbonyl, $(C_1\text{-}C_6)$alkyl, $(C_6\text{-}C_{10})$aryl or $(C_1\text{-}C_{10})$heteroaryl; wherein each of the aforesaid $(C_1\text{-}C_6)$alkylcarbonyl, $(C_1\text{-}C_6)$alkyl, $(C_6\text{-}C_{10})$aryl, and $(C_1\text{-}C_{10})$heteroaryl groups is independently optionally substituted with 1-3 substituents independently selected from halogen, $(C_1\text{-}C_6)$alkyl and $(C_1\text{-}C_6)$alkoxy;

each $R^6$ and $R^7$ is independently H, $(C_1\text{-}C_6)$alkyl, —$(CR^{10}R^{11})_t(C_6\text{-}C_{10})$aryl, —$(CR^{10}OR^{11})_t(C_1\text{-}C_{10})$heterocyclic, $(CR^{10}R^{11})_t O(CR^{10}R^{11})_t OR^{10}$, or —$(CR^{10}R^{11})_t OR^{10}$, or $R^6$ and $R^7$ taken together on the same $R^8$ or on the same $R^{12}$ can form a heteroaryl or a heterocycloalkyl group; wherein t and q are defined as set forth above and the $(C_1\text{-}C_6)$alkyl, $(C_6\text{-}C_{10})$aryl and $(C_1\text{-}C_{10})$heterocyclic moieties of the foregoing $R^6$ and $R^7$ groups are optionally substituted by 1 to 3 substituents independently selected from halo, cyano, trifluoromethyl, —$C(O)R^9$, —$NR^{10}OC(O)R^{11}$, —$C(O)NR^{10}R^{11}$, —$NR^{10}R^{11}$, $(C_1\text{-}C_6)$alkyl, —$(CR^{10}R^{11})_t(C_6\text{-}C_{10})$aryl, —$(CR^{10}R^{11})_t(C_{1\text{-}C_{10}})$heterocyclic, —$(CR^{10}R^{11})_t O(CR^{10}R^{11})_q OR^{10}$, and —$(CR^{10}R^{11})_t OR^{10}$; wherein t and q are defined as set forth above, and further that where $R^6$ and $R^7$ are both attached to the same nitrogen, then $R^6$ and $R^7$ are not both bonded to the nitrogen directly through an oxygen;

each $R^8$ and $R^{12}$ is independently halo, cyano, trifluoromethoxy, trifluoromethyl, —$C(O)R^9$, —$NR^6C(O)R^7$, —$C(O)NR^6R^7$, —$NR^6R^7$, $OR^{10}$, —$SO_2NR^6R^7$, $SO_2R^6$, —$SO_2R^6$, —$NR^6SO_2R^7$, $(C_1\text{-}C_6)$alkyl, $(C_2\text{-}C_6)$alkenyl, $(C_2\text{-}C_6)$alkynyl, —$(CR^{10}R^{11})_j O(CR^{10}R^{11})_q NR^6R^7$, —$(CR^{10}R^{11})_j O(CR^{10}R^{11})_q OR^{10}$, —$(CR^{10}R^{11})_t OR^{10}$, —$S(O)_j(C_1\text{-}C_6)$alkyl, —$(CR^{10}R^{11})_t(C_6\text{-}C_{10})$aryl, —$(CR^{10}OR^{11})_t(C_1\text{-}C_{10})$heterocyclic, —$(CR^{10}R^{11})_t O(CH_2)_q (C_1\text{-}C_{10})$heterocyclic, —$C(O)(CR^{10}R^{11})_t(C_1\text{-}C_{10})$heterocyclic, —$(CR^{10}R^{11})_j NR^7(CR^{10}R^{11})_q NR^6R^7$, —$(CR^{10}R^{11})_j NR^7CR^{10}R^{11}C(O)NR^6R^7$, —$(CR^{10}R^{11})_j NR^7 (CR^{10}R^{11})_q NR^{10}C(O)R^9$, —$(CR^{10}R^{11})_j NR^7(CR^{10}R^{11})_t O(CR^{10}R^{11})_q OR^{10}$, —$(CR^{10}R^{11})_j NR^7(CR^{10}R^{11})_q S(O)_j(C_1\text{-}C_6)$alkyl, —$(CR^{10}R^{11})_j NR^7(CR^{10}R^{11})_t R^6$, —$SO_2(CR^{10}R^{11})_t(C_6\text{-}C_{10})$aryl, or —$SO_2(CR^{10}R^{11})_t(C_1\text{-}C_{10})$heterocyclic; wherein j is independently an integer from 0 to 2; t is independently an integer from 0 to 6; q is independently an integer from 2 to 6; the —$(CR^{10}R^{11})_q$— and —$(CR^{10}R^{11})_t$— moieties of the foregoing $R^8$ and $R^{12}$ groups optionally include a carbon-carbon double or triple bond where t is an integer from 2 to 6; and the $(C_1\text{-}C_6)$alkyl, $(C_6\text{-}C_{10})$aryl and $(C_1-C_{10})$heterocyclic moieties of the aforesaid $R^8$ and $R^{12}$ groups are optionally substituted on a carbon atom by 1 to 3 substituents independently selected from halo, cyano, trifluoromethyl, —C(O)$R^9$, —N$R^6$C(O)$R^7$, —C(O)N$R^6R^7$, —(C$R^{10}R^{11}$)$_t$N$R^6R^7$, —SO$_2R^6$, —SO$_2$N$R^6R^7$, $(C_1-C_6)$alkyl, —(C$R^{10}R^{11}$)$_t(C_1-C_{10})$heterocyclic, —(C$R^{10}R^{11}$)$_t$O(C$R^{10}R^{11}$)$_q$O$R^{10}$, and —(C$R^{10}R^{11}$)$_t$O$R^{10}$;

each $R^9$ is independently H, $(C_1-C_{10})$alkyl, —(C$R^{10}R^{11}$)$_t(C_6-C_{10})$aryl, or —(C$R^{10}R^{11}$)$_t(C_1-C_{10})$heterocyclic, wherein t is defined as set forth above; and each $R^{10}$ and $R^{11}$ is independently H and $(C_1-C_6)$alkyl.

One embodiment of the invention relates to those compounds of formula 1 wherein X is HN, $(C_1-C_6)$alkyl-N—, or $(C_3-C_8)$cycloalkyl-N—.

Another embodiment of the invention relates to those compounds of formula 1, wherein X is O.

A preferred embodiment of the invention relates to those compounds of formula 1, wherein X is NH.

Another embodiment of the invention relates to those compounds of formula 1, wherein X is S.

Another embodiment of the invention relates to those compounds of formula 1 wherein L is —(CH$_2$)$_p$—, wherein p is an integer from 0 to 5; —O—; —S—; —S(O)—; —S(O)$_2$—; —N(R)—; —N(C(O)OR)—; —N(C(O)R)—; —N(S(O)$_2$R)—; —N(R)C(O)—; —N(R)S(O)—; —N(R)S(O)$_2$—; —OC(O)N(R)—; —N(R)C(O)N(R)—; —N(R)C(O)$_2$—; —OC(O)N(R)—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —S(O)N(C(O)R)—; —S(O)$_2$N(C(O)R)—; —N(R)S(O)N(R)—; —N(R)S(O)$_2$N(R)—; or —C(O)O—; and wherein each R is independently H, $(C_1-C_6)$alkylcarbonyl, $(C_1-C_6)$alkyl, $(C_6-C_{10})$aryl or $(C_1-C_{10})$heteroaryl, wherein each of the aforementioned $(C_1-C_6)$alkylcarbonyl, $(C_1-C_6)$alkyl, $(C_6-C_{10})$aryl and $(C_1-C_{10})$heteroaryl groups is independently optionally substituted with 1-3 halogens, $(C_1-C_6)$alkyl and $(C_1-C_6)$alkoxy.

Another embodiment of the invention relates to those compounds of formula 1 wherein L is —O—; —S—; —S(O)$_2$—; —N(R)—; —N(C(O)R)—; —N(S(O)$_2$R); —N(R)C(O)—; —N(R)S(O)$_2$—; —N(R)C(O)N(R)—; —S(O)$_2$N(R)—; —N(C(O)R)S(O)$_2$—; —N(R)S(O)$_2$N(R)—; —C(O)N(R)C(O)—; —S(O)$_2$N(R)C(O)—; —OS(O)$_2$N(R)—; —N(R)S(O)$_2$O—;—N(R)S(O)$_2$C(O)—; —S(O)$_2$N(C(O)R)—; —N(R)S(O)$_2$N(R)—; or —C(O)O—; and wherein each R is independently H, $(C_1-C_6)$alkylcarbonyl, $(C_1-C_6)$alkyl, $(C_6-C_{10})$aryl, or $(C_1-C_{10})$heteroaryl, wherein each of the aforementioned $(C_1-C_6)$alkylcarbonyl, $(C_1-C_6)$alkyl, $(C_6-C_{10})$aryl, and $(C_1-C_{10})$heteroaryl groups is independently optionally substituted with 1-3 halogens, $(C_1-C_6)$alkyl and $(C_1-C_6)$alkoxy.

Another embodiment of the invention relates to those compounds of formula 1 wherein L is —N(S(O)$_2$R)— or —N(R)C(O)N(R)— and wherein each R is independently H, $(C_1-C_6)$alkylcarbonyl, $(C_1-C_6)$alkyl, $(C_6-C_{10})$aryl or $(C_1-C_{10})$heteroaryl, wherein each of the aforementioned $(C_1-C_6)$alkylcarbonyl, $(C_1-C_6)$alkyl, $(C_6-C_{10})$aryl, and $(C_1-C_{10})$heteroaryl groups are independently optionally substituted with 1-3 halogens, $(C_1-C_6)$alkyl and $(C_1-C_6)$alkoxy.

Another embodiment of the invention relates to those compounds of formula 1 wherein L is —N(R)C(O)N(R)— and wherein each R is independently H or $(C_1-C_6)$alkyl.

Another embodiment of the invention relates to those compounds of formula 1 wherein L is —N(S(O)$_2$R)— and wherein R is H or $(C_1-C_6)$alkyl.

Another embodiment of the invention relates to those compounds of formula 1 wherein each embodiment of L is combined with each embodiment of X. Thus, for example, one embodiment of the present invention relates to those compounds of formula 1 wherein L is —N(R)S(O)$_2$— in combination with each of the aforesaid embodiments for X (i.e., wherein X is HN, $(C_1-C_6)$alkyl-N, $(C_3-C_8)$cycloalkyl-N, O and S. Another embodiment of the invention relates to those compounds of formula 1 wherein L is —N(R)C(O)N(R)— in combination with each of the aforesaid embodiments for X. An especially preferred embodiment of the present invention relates to those compounds of formula 1 wherein L is —N(R)S(O)$_2$— wherein R is H and X is NH. Another especially preferred embodiment of the present invention relates to those compounds of formula 1 wherein L is —N(R)C(O)N(R)— wherein R is H and X is NH.

A preferred embodiment of the invention relates to those compounds of formula 1 wherein formula 1 is represent by formula 2

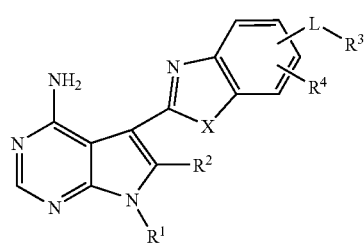

Another embodiment of the present invention relates to those compounds of formula 1 wherein $R^{10}$ is H, $(C_1-C_6)$alkyl, $(C_3-C_8)$cycloalkyl or $(C_1-C_{10})$heterocycloalkyl, wherein each of the aforesaid $(C_1-C_6)$alkyl, $(C_3-C_8)$cycloalkyl, and $(C_1-C_{10})$heterocycloalkyl groups is optionally independently substituted with 1 to 5 $(C_1-C_6)$alkyl groups.

Another embodiment of the present invention relates to those compounds of formula 1 wherein $R^1$ is H, $(C_1-C_6)$alkyl, or $(C_3-C_8)$cycloalkyl, wherein each of the aforesaid $(C_1-C_6)$alkyl and $(C_3-C_8)$cycloalkyl groups is optionally independently substituted with 1 to 5 $(C_1-C_6)$alkyl groups.

Another embodiment of the present invention relates to those compounds of formula 1 wherein $R^1$ is $(C_1-C_6)$alkyl, or $(C_3-C_8)$cycloalkyl, wherein each of the aforesaid $(C_1-C_6)$alkyl and $(C_3-C_8)$cycloalkyl groups is optionally independently substituted with 1 to 5 $(C_1-C_6)$alkyl groups.

Another embodiment of the present invention relates to those compounds of formula 1 wherein $R^1$ is $(C_3-C_8)$cycloalkyl which is optionally independently substituted with 1 to 5 $(C_1-C_6)$alkyl groups.

Another embodiment of the present invention relates to those compounds of formula 1 wherein $R^2$ is H, halo, $(C_1-C_6)$alkyl, $(C_3-C_8)$cycloalkyl, —(C$R^{10}R^{11}$)$_n$N$R^6R^7$ or —(C$R^{10}R^{11}$)$_n$C(O)N$R^9R^{10}$, wherein each of the aforesaid $(C_1-C_6)$alkyl and $(C_3-C_8)$cycloalkyl groups is optionally substituted with 1 to 5 $R^8$ substituents.

Another embodiment of the present invention relates to those compounds of formula 1 wherein $R^2$ is H, halo, and $(C_1-C_6)$alkyl, wherein the $(C_1-C_6)$alkyl group is optionally independently substituted with 1 to 5 $R^8$ substituents.

Another embodiment of the present invention relates to those compounds of formula 1 wherein each of the embodiments of $R^1$ is combined with each of the embodiments of $R^2$. Thus, for example, one embodiment of the present invention relates to those compounds of formula 1 wherein $R^1$ is $(C_1$-

$C_6$)alkyl in combination each of the aforesaid embodiments of $R^2$ (i.e., wherein $R^2$ is H, halo, ($C_1$-$C_6$)alkyl, ($C_3$-$C_8$)cycloalkyl, ($C_6$-$C_{10}$)aryl, ($C_1$-$C_{10}$)heteroaryl, ($C_3$-$C_8$)heterocycloalkyl, —($CR^{10}R^{11}$)$_n$$NR^6R^7$ or —($CR^{10}R^{11}$)$_n$$C(O)NR^6R^7$; wherein n is independently an integer from 0-3; and each of the aforesaid ($C_1$-$C_6$)alkyl, ($C_3$-$C_8$)cycloalkyl, ($C_6$-$C_{10}$)aryl, ($C_1$-$C_{10}$)heteroaryl, ($C_3$-$C_8$)heterocycloalkyl, —($CH_2$)$_n$$NR^6R^7$ and —($CH_2$)$_n$$C(O)NR^6R^7$ groups of the foregoing $R^2$ substitutent is optionally independently substituted with 1 to 5 $R^8$ substituents). An especially preferred embodiment of the present invention relates to those compounds of formula 1 wherein $R^1$ is ($C_3$-$C_8$)cycloalkyl (e.g., cyclopentyl) and $R^2$ is hydrogen. Another especially preferred embodiment of the present invention relates to those compounds of formula 1 wherein $R^1$ is ($C_1$-$C_6$)alkyl (e.g., methyl) and $R^2$ is hydrogen.

Another embodiment of the present invention relates to those compounds of formula 1, wherein $R^3$ is ($C_3$-$C_8$)cycloalkyl, —($CR^{10}R^{11}$)$_t$($C_6$-$C_{10}$,)aryl, —($CR^{10}R^{11}$)$_t$($C_1$-$C_{10}$)heteroaryl, or ($C_3$-$C_8$)heterocycloalkyl, wherein each of the aforesaid ($C_3$-$C_8$)cycloalkyl, —($CR^{10}R^{11}$)$_t$($C_6$-$C_{10}$)aryl, —($CR^{10}R^{11}$)$_t$($C_1$-$C_{10}$)heteroaryl, and ($C_3$-$C_8$)heterocycloalkyl groups is optionally independently substituted with 1 to 5 $R^{12}$ groups.

Another embodiment of the present invention relates to those compounds of formula 1, wherein $R^3$ is ($C_3$-$C_8$)cycloalkyl, —($CR^{10}R^{11}$)$_t$($C_6$-$C_{10}$)aryl, or —($CR^{10}R^{11}$)$_t$($C_1$-$C_{10}$)heteroaryl, wherein each of the aforesaid ($C_3$-$C_8$)cycloalkyl, —($CR^{10}R^{11}$)$_2$($C_6$-$C_{10}$)aryl, and —($CR^{10}R^{11}$)$_t$($C_1$-$C_{10}$)heteroaryl groups is optionally independently substituted with 1 to 5 $R^{12}$ groups.

Another embodiment of the present invention relates to those compounds of formula 1, wherein $R^3$ is —($CR^{10}R^{11}$)$_t$($C_6$-$C_{10}$)aryl, or —($CR^{10}R^{11}$)$_t$($C_1$-$C_{10}$)heteroaryl, wherein each of the aforesaid —($CR^{10}R^{11}$)$_t$($C_6$-$C_{10}$)aryl, and —($CR^{10}R^{11}$)$_t$($C_1$-$C_{10}$)heteroaryl groups is optionally independently substituted with 1 to 5 $R^{12}$ groups.

Another embodiment of the present invention relates to those compounds of formula 1, wherein wherein each of the embodiments of $R^3$ is combined with each member of the embodiments of $R^4$. Thus, for example, one embodiment of the present invention relates to those compounds of formula 1 wherein $R^3$ is —($CR^{10}R^{11}$)$_t$($C_6$-$C_{10}$)aryl wherein the —($CR^{10}R^{11}$)$_t$($C_6$-$C_{10}$)aryl is optionally substituted in combination with each of the embodiments of $R^4$ (i.e., $R^4$ is H, halo, ($C_1$-$C_6$)alkyl, ($C_3$-$C_6$)cycloalkyl, ($C_1$-$C_6$)alkoxy, or ($C_3$-$C_6$)cycloalkoxy). In an especially preferred embodiment $R^3$ is —($CR^{10}R^{11}$)$_t$($C_6$-$C_{10}$)aryl wherein t is 0 (zero) and $R^4$ is H.

Another embodiment of the present invention relates to those compounds of formula 1 that are selected from the group consisting of:

N-[2-(4-Amino-7-cyclopentyl-7H-pyrrolo[2,3-d]pyrimidin-5-yl)-1H-benzoimidazol-5-yl]-2,6-difluoro-benzenesulfonamide;

N-[2-(4-Amino-7-cyclopentyl-7H-pyrrolo[2,3-d]pyrimidin-5-yl)-3H-benzoimidazol-5-yl]-2,4-difluoro-benzenesulfonamide;

5-(6-Amino-1H-benzoimidazol-2-yl)-7-cyclopentyl-7H-pyrrolo[2,3-d]pyrimidin-4-ylamine;

1-[2-(4-Amino-7-cyclopentyl-7H-pyrrolo[2,3-d]pyrimidin-5-yl)-3H-benzoimidazol-5-yl]-3-p-tolyl-urea;

1-[2-(4-Amino-7-cyclopentyl-7H-pyrrolo[2,3-d]pyrimidin-5-yl)-3H-benzoimidazol-5-yl]-3-m-tolyl-urea;

1-[2-(4-Amino-7-cyclopentyl-7H-pyrrolo[2,3-d]pyrimidin-5-yl)-3H-benzoimidazol-5-yl]-3-(2-fluoro-phenyl)-urea;

1-[2-(4-Amino-7-cyclopentyl-7H-pyrrolo[2,3-d]pyrimidin-5-yl)-3H-benzoimidazol-5-yl]-3-(3-ethyl-phenyl)-urea;

1-[2-(4-Amino-7-cyclopentyl-7H-pyrrolo[2,3-d]pyrimidin-5-yl)-3H-benzoimidazol-5-yl]-3-(2-methoxy-phenyl)-urea;

1-[2-(4-Amino-7-cyclopentyl-7H-pyrrolo[2,3-d]pyrimidin-5-yl)-3H-benzoimidazol-5-yl]-3-(3-methoxy-phenyl)-urea;

1-[2-(4-Amino-7-cyclopentyl-7H-pyrrolo[2,3-d]pyrimidin-5-yl)-3H-benzoimidazol-5-yl]-3-(4-methoxy-phenyl)-urea;

1-[2-(4-Amino-7-cyclopentyl-7H-pyrrolo[2,3-d]pyrimidin-5-yl)-3H-benzoimidazol-5-yl]-3-(2-fluoro-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-chloro-phenyl)-urea;

1-[2-(4-Amino-7-cyclopentyl-7H-pyrrolo[2,3-d]pyrimidin-5-yl)-3H-benzoimidazol-5-yl]-3-(4-chloro-phenyl)-urea;

1-[2-(4-Amino-7-cyclopentyl-7H-pyrrolo[2,3-d]pyrimidin-5-yl)-3H-benzoimidazol-5-yl]-3-(3,5-difluoro-phenyl)-urea;

1-[2-(4-Amino-7-cyclopentyl-7H-pyrrolo[2,3-d]pyrimidin-5-yl)-3H-benzoimidazol-5-yl]-3-(3,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2,5-difluoro-phenyl)-urea;

1-[2-(4-Amino-7-cyclopentyl-7H-pyrrolo[2,3-d]pyrimidin-5-yl)-3H-benzoimidazol-5-yl]-3-(2,6-difluoro-phenyl)-urea;

1-[2-(4-Amino-7-cyclopentyl-7H-pyrrolo[2,3-d]pyrimidin-5-yl)-3H-benzoimidazol-5-yl]-3-(2,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2-methoxy-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-ethoxy-phenyl)-urea;

N-[2-(4-Amino-7-cyclopentyl-7H-pyrrolo[2,3-d]pyrimidin-5-yl)-3H-benzoimidazol-5-yl]-4-ethyl-benzenesulfonamide;

N-[2-(4-Amino-7-cyclopentyl-7H-pyrrolo[2,3-d]pyrimidin-5-yl)-3H-benzoimidazol-5-yl]-4-methoxy-benzenesulfonamide;

N-[2-(4-Amino-7-cyclopentyl-7H-pyrrolo[2,3-d]pyrimidin-5-yl)-3H-benzoimidazol-5-yl]-4-chloro-benzenesulfonamide;

N-[2-(4-Amino-7-cyclopentyl-7H-pyrrolo[2,3-d]pyrimidin-5-yl)-3H-benzoimidazol-5-yl]-2-chloro-benzenesulfonamide;

N-[2-(4-Amino-7-cyclopentyl-7H-pyrrolo[2,3-d]pyrimidin-5-yl)-3H-benzoimidazol-5-yl]-2,5-difluoro-benzenesulfonamide;

N-[2-(4-Amino-7-cyclopentyl-7H-pyrrolo[2,3-d]pyrimidin-5-yl)-3H-benzoimidazol-5-yl]-3,4-difluoro-benzenesulfonamide;

N-[2-(4-Amino-7-cyclopentyl-7H-pyrrolo[2,3-d]pyrimidin-5-yl)-3H-benzoimidazol-5-yl]-2-methoxy-4-methyl-benzenesulfonamide;

N-[2-(4-Amino-7-cyclopentyl-7H-pyrrolo[2,3-d]pyrimidin-5-yl)-3H-benzoimidazol-5-yl]-3-chloro-2-methyl-benzenesulfonamide;

N-[2-(4-Amino-7-cyclopentyl-7H-pyrrolo[2,3-d]pyrimidin-5-yl)-3H-benzoimidazol-5-yl]-3-chloro-4-methyl-benzenesulfonamide;

N-[2-(4-Amino-7-cyclopentyl-7H-pyrrolo[2,3-d]pyrimidin-5-yl)-3H-benzoimidazol-5-yl]-3-chloro-4-fluoro-benzenesulfonamide;

N-[2-(4-Amino-7-cyclopentyl-7H-pyrrolo[2,3-d]pyrimidin-5-yl)-3H-benzoimidazol-5-yl]-5-chloro-2-methoxy-benzenesulfonamide;

N-[2-(4-Amino-7-cyclopentyl-7H-pyrrolo[2,3-d]pyrimidin-5-yl)-3H-benzoimidazol-5-yl]-3,5-dichloro-benzenesulfonamide;

N-[2-(4-Amino-7-cyclopentyl-7H-pyrrolo[2,3-d]pyrimidin-5-yl)-3H-benzoimidazol-5-yl]-2,4-dichloro-benzenesulfonamide;

Biphenyl-3-sulfonic acid [2-(4-amino-7-cyclopentyl-7H-pyrrolo[2,3-d]pyrimidin-5-yl)-3H-benzoimidazol-5-yl]-amide;

N-[2-(4-Amino-7-cyclopentyl-7H-pyrrolo[2,3-d]pyrimidin-5-yl)-3H-benzoimidazol-5-yl]-2-trifluoromethoxy-benzenesulfonamide;

N-[2-(4-Amino-7-cyclopentyl-7H-pyrrolo[2,3-d]pyrimidin-5-yl)-3H-benzoimidazol-5-yl]-3-(pyridin-2-yloxy)-benzenesulfonamide;

1-[2-(4-Amino-7-cyclopentyl-7H-pyrrolo[2,3-d]pyrimidin-5-yl)-benzothiazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-methoxy-5-methyl-phenyl)-urea;

1-[2-(4-Amino-7-cyclopentyl-7H-pyrrolo[2,3-d]pyrimidin-5-yl)-benzothiazol-6-yl]-3-(2-methoxy-5-methyl-phenyl)-urea;

1-[2-(4-Amino-7-cyclopentyl-7H-pyrrolo[2,3-d]pyrimidin-5-yl)-benzooxazol-6-yl]-3-(2,6-difluoro-phenyl)-urea;

1-[2-(4-Amino-7-cyclopentyl-7H-pyrrolo[2,3-d]pyrimidin-5-yl)-benzothiazol-6-yl]-3-(2,6-difluoro-phenyl)-urea;

1-[2-(4-Amino-7-cyclopentyl-7H-pyrrolo[2,3-d]pyrimidin-5-yl)-benzooxazol-6-yl]-3-m-tolyl-urea;

1-[2-(4-Amino-7-cyclopentyl-7H-pyrrolo[2,3-d]pyrimidin-5-yl)-benzothiazol-6-yl]-3-m-tolyl-urea;

1-[2-(4-Amino-7-cyclopentyl-7H-pyrrolo[2,3-d]pyrimidin-5-yl)-benzooxazol-6-yl]-3-(3-ethyl-phenyl)-urea;

1-[2-(4-Amino-7-cyclopentyl-7H-pyrrolo[2,3-d]pyrimidin-5-yl)-benzothiazol-6-yl]-3-(3-ethyl-phenyl)-urea;

and the pharmaceutically acceptable salt, prodrug, hydrate or solvate of the aforementioned compounds.

Another embodiment of the present invention relates to those compounds of formula 1 that are selected from the group consisting of:

N-[2-(4-Amino-7-cyclopentyl-7H-pyrrolo[2,3-d]pyrimidin-5-yl)-1H-benzoimidazol-5-yl]-2,6-difluoro-benzenesulfonamide;

N-[2-(4-Amino-7-cyclopentyl-7H-pyrrolo[2,3-d]pyrimidin-5-yl)-3H-benzoimidazol-5-yl]-2,4-difluoro-benzenesulfonamide;

1-[2-(4-Amino-7-cyclopentyl-7H-pyrrolo[2,3-d]pyrimidin-5-yl)-3H-benzoimidazol-5-yl]-3-p-tolyl-urea;

1-[2-(4-Amino-7-cyclopentyl-7H-pyrrolo[2,3-d]pyrimidin-5-yl)-3H-benzoimidazol-5-yl]-3-m-tolyl-urea;

1-[2-(4-Amino-7-cyclopentyl-7H-pyrrolo[2,3-d]pyrimidin-5-yl)-3H-benzoimidazol-5-yl]-3-(2-fluoro-phenyl)-urea;

1-[2-(4-Amino-7-cyclopentyl-7H-pyrrolo[2,3-d]pyrimidin-5-yl)-3H-benzoimidazol-5-yl]-3-(3-ethyl-phenyl)-urea;

1-[2-(4-Amino-7-cyclopentyl-7H-pyrrolo[2,3-d]pyrimidin-5-yl)-3H-benzoimidazol-5-yl]-3-(2-methoxy-phenyl)-urea;

1-[2-(4-Amino-7-cyclopentyl-7H-pyrrolo[2,3-d]pyrimidin-5-yl)-3H-benzoimidazol-5-yl]-3-(3-methoxy-phenyl)-urea;

1-[2-(4-Amino-7-cyclopentyl-7H-pyrrolo[2,3-d]pyrimidin-5-yl)-3H-benzoimidazol-5-yl]-3-(4-methoxy-phenyl)-urea;

1-[2-(4-Amino-7-cyclopentyl-7H-pyrrolo[2,3-d]pyrimidin-5-yl)-3H-benzoimidazol-5-yl]-3-(2-fluoro-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-chloro-phenyl)-urea;

1-[2-(4-Amino-7-cyclopentyl-7H-pyrrolo[2,3-d]pyrimidin-5-yl)-3H-benzoimidazol-5-yl]-3-(4-chloro-phenyl)-urea;

1-[2-(4-Amino-7-cyclopentyl-7H-pyrrolo[2,3-d]pyrimidin-5-yl)-3H-benzoimidazol-5-yl]-3-(3,5-difluoro-phenyl)-urea;

1-[2-(4-Amino-7-cyclopentyl-7H-pyrrolo[2,3-d]pyrimidin-5-yl)-3H-benzoimidazol-5-yl]-3-(3,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2,5-difluoro-phenyl)-urea;

1-[2-(4-Amino-7-cyclopentyl-7H-pyrrolo[2,3-d]pyrimidin-5-yl)-3H-benzoimidazol-5-yl]-3-(2,6-difluoro-phenyl)-urea;

1-[2-(4-Amino-7-cyclopentyl-7H-pyrrolo[2,3-d]pyrimidin-5-yl)-3H-benzoimidazol-5-yl]-3-(2,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2-methoxy-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-ethoxy-phenyl)-urea;

N-[2-(4-Amino-7-cyclopentyl-7H-pyrrolo[2,3-d]pyrimidin-5-yl)-3H-benzoimidazol-5-yl]-2-chloro-benzenesulfonamide;

N-[2-(4-Amino-7-cyclopentyl-7H-pyrrolo[2,3-d]pyrimidin-5-yl)-3H-benzoimidazol-5-yl]-2,5-difluoro-benzenesulfonamide;

1-[2-(4-Amino-7-cyclopentyl-7H-pyrrolo[2,3-d]pyrimidin-5-yl)-benzothiazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-methoxy-5-methyl-phenyl)-urea;

1-[2-(4-Amino-7-cyclopentyl-7H-pyrrolo[2,3-d]pyrimidin-5-yl)-benzothiazol-6-yl]-3-(2-methoxy-5-methyl-phenyl)-urea;

1-[2-(4-Amino-7-cyclopentyl-7H-pyrrolo[2,3-d]pyrimidin-5-yl)-benzooxazol-6-yl]-3-(2,6-difluoro-phenyl)-urea;

1-[2-(4-Amino-7-cyclopentyl-7H-pyrrolo[2,3-d]pyrimidin-5-yl)-benzothiazol-6-yl]-3-(2,6-difluoro-phenyl)-urea;

1-[2-(4-Amino-7-cyclopentyl-7H-pyrrolo[2,3-d]pyrimidin-5-yl)-benzooxazol-6-yl]-3-m-tolyl-urea;

1-[2-(4-Amino-7-cyclopentyl-7H-pyrrolo[2,3-d]pyrimidin-5-yl)-benzothiazol-6-yl]-3-m-tolyl-urea;

1-[2-(4-Amino-7-cyclopentyl-7H-pyrrolo[2,3-d]pyrimidin-5-yl)-benzooxazol-6-yl]-3-(3-ethyl-phenyl)-urea;

1-[2-(4-Amino-7-cyclopentyl-7H-pyrrolo[2,3-d]pyrimidin-5-yl)-benzothiazol-6-yl]-3-(3-ethyl-phenyl)-urea;

and the pharmaceutically acceptable salt, prodrug, hydrate or solvate of the aforementioned compounds.

Another embodiment of the present invention relates to those compounds of formula 1 that are selected from the group consisting of:

N-[2-(4-Amino-7-cyclopentyl-7H-pyrrolo[2,3-d]pyrimidin-5-yl)-1H-benzoimidazol-5-yl]-2,6-difluoro-benzenesulfonamide;

N-[2-(4-Amino-7-cyclopentyl-7H-pyrrolo[2,3-d]pyrimidin-5-yl)-3H-benzoimidazol-5-yl]-2,4-difluoro-benzenesulfonamide;

1-[2-(4-Amino-7-cyclopentyl-7H-pyrrolo[2,3-d]pyrimidin-5-yl)-3H-benzoimidazol-5-yl]-3-m-tolyl-urea;

1-[2-(4-Amino-7-cyclopentyl-7H-pyrrolo[2,3-d]pyrimidin-5-yl)-3H-benzoimidazol-5-yl]-3-(2-fluoro-phenyl)-urea;

1-[2-(4-Amino-7-cyclopentyl-7H-pyrrolo[2,3-d]pyrimidin-5-yl)-3H-benzoimidazol-5-yl]-3-(3-ethyl-phenyl)-urea;

1-[2-(4-Amino-7-cyclopentyl-7H-pyrrolo[2,3-d]pyrimidin-5-yl)-3H-benzoimidazol-5-yl]-3-(3-methoxy-phenyl)-urea;

1-[2-(4-Amino-7-cyclopentyl-7H-pyrrolo[2,3-d]pyrimidin-5-yl)-3H-benzoimidazol-5-yl]-3-(4-methoxy-phenyl)-urea;

1-[2-(4-Amino-7-cyclopentyl-7H-pyrrolo[2,3-d]pyrimidin-5-yl)-3H-benzoimidazol-5-yl]-3-(2-fluoro-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-chloro-phenyl)-urea;

1-[2-(4-Amino-7-cyclopentyl-7H-pyrrolo[2,3-d]pyrimidin-5-yl)-3H-benzoimidazol-5-yl]-3-(2,6-difluoro-phenyl)-urea;

1-[2-(4-Amino-7-cyclopentyl-7H-pyrrolo[2,3-d]pyrimidin-5-yl)-3H-benzoimidazol-5-yl]-3-(2,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2-methoxy-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-ethoxy-phenyl)-urea;

1-[2-(4-Amino-7-cyclopentyl-7H-pyrrolo[2,3-d]pyrimidin-5-yl)-benzothiazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-methoxy-5-methyl-phenyl)-urea;

1-[2-(4-Amino-7-cyclopentyl-7H-pyrrolo[2,3-d]pyrimidin-5-yl)-benzothiazol-6-yl]-3-(2-methoxy-5-methyl-phenyl)-urea;

1-[2-(4-Amino-7-cyclopentyl-7H-pyrrolo[2,3-d]pyrimidin-5-yl)-benzooxazol-6-yl]-3-(2,6-difluoro-phenyl)-urea;

1-[2-(4-Amino-7-cyclopentyl-7H-pyrrolo[2,3-d]pyrimidin-5-yl)-benzothiazol-6-yl]-3-(2,6-difluoro-phenyl)-urea;

1-[2-(4-Amino-7-cyclopentyl-7H-pyrrolo[2,3-d]pyrimidin-5-yl)-benzooxazol-6-yl]-3-m-tolyl-urea;

1-[2-(4-Amino-7-cyclopentyl-7H-pyrrolo[2,3-d]pyrimidin-5-yl)-benzothiazol-6-yl]-3-m-tolyl-urea;

1-[2-(4-Amino-7-cyclopentyl-7H-pyrrolo[2,3-d]pyrimidin-5-yl)-benzooxazol-6-yl]-3-(3-ethyl-phenyl)-urea;

1-[2-(4-Amino-7-cyclopentyl-7H-pyrrolo[2,3-d]pyrimidin-5-yl)-benzothiazol-6-yl]-3-(3-ethyl-phenyl)-urea;

and the pharmaceutically acceptable salt, prodrug, hydrate or solvate of the aforementioned compounds.

The present invention also relates to a pharmaceutical composition for the treatment of abnormal cell growth in a mammal which an amount of a compound of formula 1 or a pharmaceutically acceptable salt, prodrug, solvate or hydrate thereof that is effective in treating abnormal cell growth, and a pharmaceutically acceptable carrier. In one embodiment, said abnormal cell growth is cancer. In another embodiment, said abnormal cell growth is a non-cancerous hyperproliferative disorder, such as benign hyperplasia of the skin (e.g., psoriasis) or prostate (e.g., benign prostatic hypertrophy (BPH)).

In another embodiment of the present invention, said cancer is selected from the group consisting of lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In one preferred embodiment the cancer is selected from the group consisting of brain, squamous cell, bladder, gastric, pancreatic, breast, head, neck, oesophageal, prostate, colorectal, lung, renal, kidney, ovarian, gynecological and thyroid cancer.

In a more preferred embodiment the cancer is selected from the group consisting of prostate, breast, lung, colon and ovarian cancer.

In another more preferred embodiment the cancer is selected from the group consisting of prostate, breast, and lung cancer.

In a most preferred embodiment the breast cancer is metastatic breast cancer.

In a most preferred embodiment the lung cancer is non-small cell lung cancer.

The present invention also relates to a pharmaceutical composition for the treatment of pancreatitis or kidney disease (such as proliferative glomerulonephritis and diabetes-induced renal disease) in a mammal which comprises an amount of a compound of formula 1 or a pharmaceutically acceptable salt, prodrug, solvate or hydrate thereof that is effective in treating said pancreatitis or kidney disease, and a pharmaceutically acceptable carrier.

The present invention also relates to a pharmaceutical composition for the prevention of blastocyte implantation in a mammal which comprises an amount of a compound of formula 1, or a pharmaceutically acceptable salt, prodrug or hydrate thereof that is effective in preventing said blastocyte implantation and a pharmaceutically acceptable carrier.

The present invention also relates to a pharmaceutical composition for treating a disease related to vasculogenesis or angiogenesis in a mammal which comprises an amount of a compound of formula 1, or a pharmaceutically acceptable salt, prodrug or hydrate thereof that is effective in treating said disease, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method for the treatment of abnormal cell growth in a mammal which comprises administering to said mammal an amount of the compound of formula 1, or a pharmaceutically acceptable salt, prodrug or hydrate thereof that is effective in treating said abnormal cell growth. In one embodiment, said method relates to the treatment of cancer such as lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers. In one preferred embodiment the cancer is selected from the group consisting of brain, squamous cell, bladder, gastric, pancreatic, breast, head, neck, oesophageal, prostate, colorectal, lung, renal, kidney, ovarian, gynecological and thyroid cancer. In a more preferred embodiment the cancer is selected from the group consisting of prostate, breast, lung, colon and ovarian cancer. In another more preferred embodiment the cancer is selected from the group consisting of prostate, breast, and lung cancer. In a most preferred embodiment the breast cancer is metastatic breast cancer. In a most preferred embodiment the lung cancer is non-small cell lung cancer.

In another embodiment, said method relates to the treatment of a non-cancerous hyperproliferative disorder such as benign hyperplasia of the skin (e.g., psoriasis) or prostate (e.g., benign prostatic hypertrophy (BPH)).

The present invention also relates to a method for the treatment of vasculogenesis, restenosis, atherosclerosis or angiogenesis in a mammal which comprises administering to said mammal an effective amount of a compound of formula 1, or a pharmaceutically acceptable salt, prodrug or hydrate thereof that is effective in treating said vasculogenesis, restenosis, atherosclerosis or angiogenesis. Preferably, said method is for the treatment of vasculogenesis or angiogenesis. In one embodiment, said method is for treating a disease selected from the group consisting of tumor angiogenesis, chronic inflammatory disease such as rheumatoid arthritis, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method for the treatment of a hyperproliferative disorder in a mammal which comprises administering to said mammal a therapeutically effective amount of a compound of formula 1, or a pharmaceutically acceptable salt, prodrug or hydrate thereof, in combination with an anti-tumor agent selected from the group consisting of, but not limited to, mitotic inhibitors, alkylating agents, cytotoxic agents (such us topoisomerase inhibitors, platinum agents) anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens.

The invention also relates to a method of treating pancreatitis or kidney disease in a mammal which comprises administering to said mammal a therapeutically effective amount of a compound of formula 1,or a pharmaceutically acceptable salt, prodrug or hydrate thereof.

The invention also relates to a method of preventing blastocyte implantation in a mammal which comprises administering to said mammal an amount of a compound of formula 1, or a pharmaceutically acceptable salt, prodrug or hydrate thereof that is effective for said prevention of blastocyte implantation.

This invention also relates to a pharmaceutical composition for inhibiting abnormal cell growth in a mammal which comprises an amount of a compound of formula 1, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal which method comprises administering to the mammal an amount of a compound of formula 1,or a pharmaceutically acceptable salt or solvate or prodrug thereof, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula 1 can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or pharmaceutically acceptable salt, prodrug or solvate thereof, which amount is effective in sensitizing abnormal cells to treatment with radiation. The amount of the compound, salt, or solvate in this method can be determined according to the means for ascertaining effective amounts of such compounds described herein.

This invention also relates to a pharmaceutical composition for inhibiting abnormal cell growth in a mammal, including a human, comprising an amount of a compound of the formula 1 as defined above, or a pharmaceutically acceptable salt, prodrug or solvate thereof, that is effective in inhibiting farnesyl protein transferase, and a pharmaceutically acceptable carrier.

This invention further relates to a pharmaceutical composition for inhibiting abnormal cell growth in a mammal comprising an amount of a compound of formula 1, or a pharmaceutically acceptable salt or solvate or prodrug thereof that is effective in inhibiting abnormal cell growth, and a pharmaceutically acceptable carrier.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

This invention also relates to a pharmaceutical composition for inhibiting abnormal cell growth in a mammal, including a human, comprising an amount of a compound of formula 1 as defined above, or a pharmaceutically acceptable salt or solvate thereof, that is effective in inhibiting farnesyl protein transferase, and a pharmaceutically acceptable carrier.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

The present invention also relates to a process for preparing a compound of the formula 1, as set forth above or a pharmaceutically acceptable salt, prodrug, solvate or hydrate thereof which comprises treating a compound of the formula 1A wherein Z is halo (such as chloro)

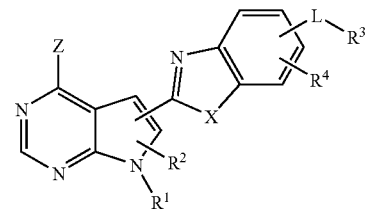

with a compound of the formula H₃N.

An embodiment of the present invention refers to those methods wherein formula 1 is represented by formula 2

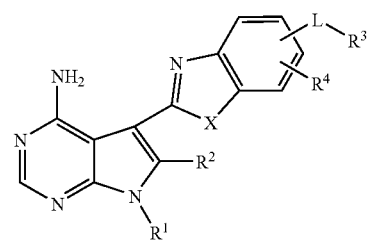

and formula 1A is represented by formula 1B

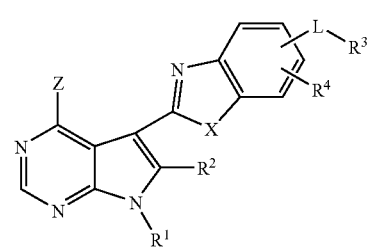

Another embodiment of the present invention refers to those methods wherein formula 1 is represented by formula 3

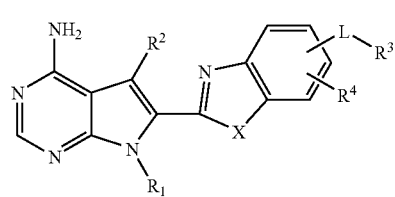

and formula 1A is represented by formula 1C

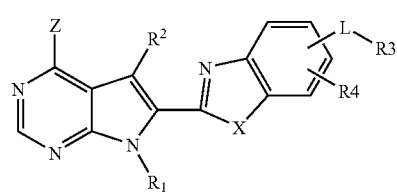

The present invention also relates to a process for preparing a compound of the formula 13

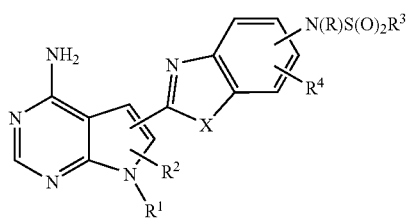

13 or a pharmaceutically acceptable salt, prodrug, solvate or hydrate thereof, wherein X, R, $R^1$, $R^2$, $R^3$ and $R^4$ have the same meaning as set forth above for formula 1, which comprises treating a compound of the formula 10A

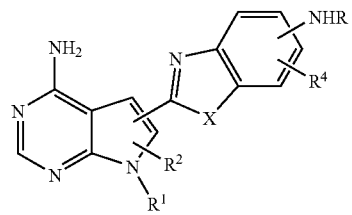

10A with a compound of formula $R^3$—S(O)$_2$—Cl, wherein $R^3$ has the same meaning as set forth above for formula 1.

The present invention also relates to a process for preparing a compound of the formula 14

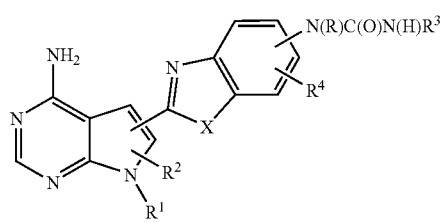

14 or a pharmaceutically acceptable salt, prodrug, solvate or hydrate thereof, wherein X, R, $R^1$, $R^2$, $R^3$ and $R^4$ have the same meaning as set forth above for formula 1, which comprises reacting a compound of the formula 10A

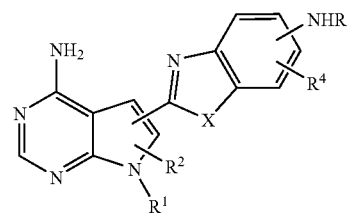

10A wherein X, R, $R^1$, $R^2$, $R^4$ have the same meaning as set forth above for formula 1, with a compound of formula $R^3$—NCO, wherein $R^3$ has the same meaning as set forth above for formula 1.

The present invention also relates to a process for preparing a compound of the formula 1D

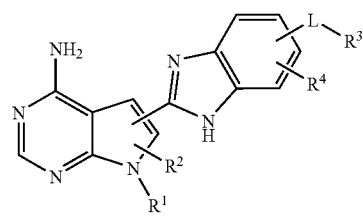

1D or a pharmaceutically acceptable salt, prodrug, solvate or hydrate thereof, wherein wherein L, R. $R^1$, $R^2$, $R^3$ and $R^4$ have the same meaning as set forth above for formula 1, which comprises treating with a compound of formula 12A

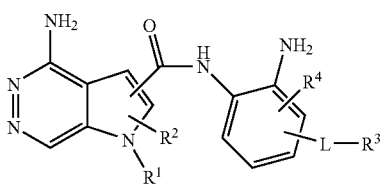

12A under acidic conditions.

In one embodiment of the process for preparing the compound of formula 1D, the compound of formula 12A is treated with acetic acid.

In another embodiment, the compound of formula 12A is prepared by reacting a compound of formula 11

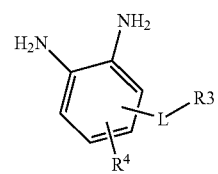

11 with a compound of formula 7A

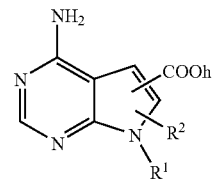

7A

Anti-angiogenesis agents, such as MMP-2 (matrix-metalloprotienase 2) inhibitors, MMP-9 (matrix-metalloproteinase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxy-carbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxy-carbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxy-carbamoyl-1-methyl-ethyl)-amino]-propionic acid;

3-[[4-(4-fluoro-phenoxy)-benzenesulfonyl]-(4-hydroxy-carbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), ABX-EGF (Abgenix/Cell Genesys), EMD-7200 (Merck KgaA), EMD-5590 (Merck KgaA), MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGFR Vaccine (York Medical/Centro de Immunologia Molecular (CIM)). These and other EGFR-inhibiting agents can be used in the present invention.

VEGF inhibitors, for example CP-547,632 and AG-13736, SU-11246, SU-5416 and SU-6668 (Pfizer Inc.), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as CP-724,714 (Pfizer, Inc.), GW-2016, GW-282974, and GW-572016 (Glaxo Wellcome plc), TAK-165 (Takeda) and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) which is incorporated by reference in its entirety; however other CTLA4 antibodies can be used in the present invention.

Other anti-angiogenesis agents, including, but not limited to, CI-1040, CI-1030 and CI-994 (all of the foregoing of Pfizer, Inc.) other COX-II inhibitors, other MMP inhibitors, other anti-VEGF antibodies or inhibitors of other effectors of vascularization can also be used in the present invention.

The subject invention also includes isotopically-labelled compounds, which are identical to those recited in formula 1 but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula 1 of this invention and prodrugs thereof can generally be prepared by carrying out the procedures disclosed in the Schemes and/or in the Examples below, by substituting a readily available isotopically labeled reagent for a non-isotopically labeled reagent.

The compounds of formula 1 and their pharmaceutically acceptable salts and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

A "suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl), and they may also be cyclic (e.g., cyclopropyl or cyclobutyl); optionally substituted by 1 to 5 suitable substituents as defined above such as fluoro, chloro, trifluoromethyl, ($C_1$-$C_6$)alkoxy, ($C_6$-$C_{10}$)aryloxy, trifluoromethoxy, difluoromethoxy or ($C_1$-$C_6$)alkyl. The phrase "each of said alkyl" as used herein refers to any of the preceding alkyl moieties within a group such alkoxy, alkenyl or alkylamino. Preferred alkyls include ($C_1$-$C_4$)alkyl, most preferably methyl.

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1-2 double bonds and optionally substituted by 1 to 3 suitable substituents as defined above such as fluoro, chloro, trifluoromethyl, ($C_1$-$C_6$)alkoxy, ($C_6$-$C_{10}$) aryloxy, trifluoromethoxy, difluoromethoxy or ($C_1$-$C_6$)alkyl. The phrase "each of said alkyl" as used herein refers to any of the preceding alkyl moieties within a group such alkoxy, alkenyl or alkylamino. Preferred cycloalkyls include cyclobutyl, cyclopentyl and cyclohexyl.

As used herein, the term "halogen" includes fluoro, chloro, bromo or iodo or fluoride, chloride, bromide or iodide.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "$(C_2-C_6)$alkynyl" is used herein to mean straight or branched hydrocarbon chain radicals having one triple bond including, but not limited to, ethynyl, propynyl, butynyl, and the like; optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "carbonyl" or "(C=O)" (as used in phrases such as alkylcarbonyl, alkyl—(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "aryl" means aromatic radicals such as phenyl, naphthyl, tetrahydronaphthyl, indanyl and the like; optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl (these heteroaryls are most preferred of the $R^4$ heteroaryls).

The term "heterocycloalkyl" as used herein means a non-aromatic monovalent ring (which can include bicyclo ring systems) having from 4 to 10 members, of which, up to 4 are heteroatoms such as N, O and S for example. The heterocycloalkyl groups of this invention can also include ring systems substituted with one or more oxo moieties. Heterocycloalkyl groups may be unsubstituted or substituted with those substituents enumerated for cycloalkyl. Examples of heterocycloalkyl groups include, but are not limited to, 2- or 3-tetrahydrothieno, 2- or 3-tetrahydrofurano, 1-, 2- or 3-pyrrolidino, 2-, 4-, or 5-thiazolidino, 2-, 4-, or 5-oxazolidino, 2-, 3-, or 4-piperidino, N-morpholinyl, N-thiamorpholinyl, 3-azabicyclo[3.1.0]hexanyl, 3-azabicyclo[4.1.0]heptanyl, 1,4-dioxaspiro[4.5]decyl, 1,4-dioxaspiro[4.4]nonyl, 1,4-dioxaspiro[4.3]octyl, and 1,4-dioxaspiro[4.2]heptyl. Examples of substituted heterocycloalkyl groups include, but are not limited to, 1-methyl-pyrrolidin-3-yl, 1-acetyl-pyrrolidin-3-yl, 1-methyl-piperidin-4-yl, 1-acetyl-piperidin-4-yl, 1-methyl-azetidin-3-yl, 1-acetyl-azetidin-3-yl, 2-oxo-piperidin-1-yl, and 2,3-Dimethyl-1,4-dioxa-spiro[4.4]nonyl.

As used herein, the phrase "heterocyclic ring" in the context of the phrase "$R^6$ and $R^7$ taken together on the same $R^8$ or on the same $R^{12}$ can form a heterocyclic ring" refers to a nonaromatic ring having from 4 to 8 members, of which at least 1 is a N atom, and up to 4 of which are heteroatoms such as N, O and S for example. The heterocyclic ring may be unsubstituted or substituted on a carbon atom with those substituents enumerated for cycloalkyl. Examples of such heterocyclic rings include pyrrolidine, piperidine, piperazine, morpholine, and thiamorpholine.

As used herein, the term "HATU" refers to O-(7-Azabenzoiriazol-1-yl)-N,N,N',N'-tetramethyluronium hexafluorophosphate.

The term "alkoxy", as used herein, unless otherwise indicated, means O-alkyl groups wherein "alkyl" is as defined above.

The term "acyl", as used herein, refers to a species containing a carbon-oxygen double bond.

The phrase "pharmaceutically acceptable salt(s)", as used herein, unless otherwise indicated, includes salts of acidic or basic groups which may be present in the compounds of formula 1,The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature are capable of forming base salts with various pharmacologically acceptable cations. Examples of such salts include the alkali metal or alkaline earth metal salts and particularly, the sodium and potassium salts.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula 1 may also exist as tautomers. This invention relates to the use of all such tautomers and mixtures thereof.

This invention also encompasses pharmaceutical compositions containing and methods of treating proliferative disorders or abnormal cell growth through administering prodrugs of compounds of the formula 1,Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1,The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

DETAILED DESCRIPTION OF THE INVENTION

The compounds of the present invention are readily prepared according to synthetic methods familiar to those skilled in the art. Scheme 1 illustrates a general synthetic sequence for preparing compounds of the present invention where X is NH, $R^2$ and $R^4$ are both hydrogen (H) atoms.

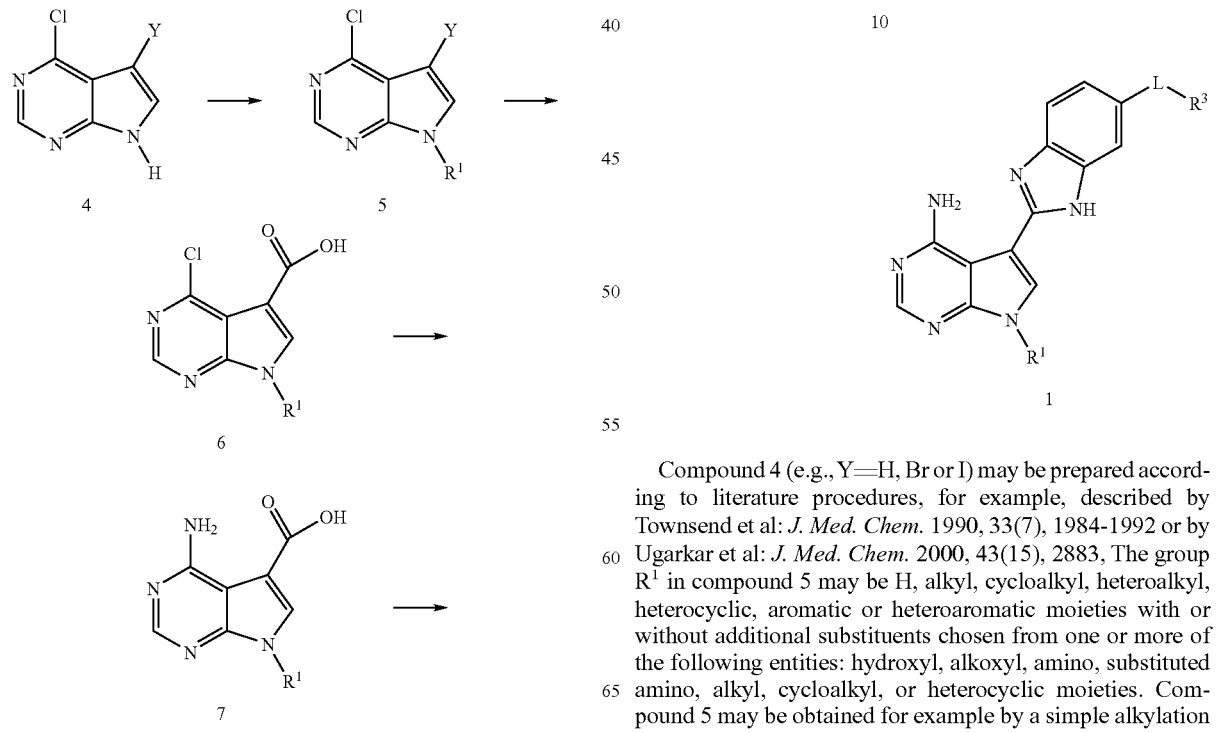

Compound 4 (e.g., Y=H, Br or I) may be prepared according to literature procedures, for example, described by Townsend et al: *J. Med. Chem.* 1990, 33(7), 1984-1992 or by Ugarkar et al: *J. Med. Chem.* 2000, 43(15), 2883, The group $R^1$ in compound 5 may be H, alkyl, cycloalkyl, heteroalkyl, heterocyclic, aromatic or heteroaromatic moieties with or without additional substituents chosen from one or more of the following entities: hydroxyl, alkoxyl, amino, substituted amino, alkyl, cycloalkyl, or heterocyclic moieties. Compound 5 may be obtained for example by a simple alkylation of 4, using for example, inorganic base in the presence of alkyl halide, or by a Mitsunobu reaction. Introduction of halogen atoms can be performed on either 4 or 5 using literature procedures, for example, described by Townsend et al: *J. Med. Chem.* 1990, 33(7), 1984-1992, Compound 5 (e.g., Y=Br) may be converted to 6 by treatment of 4 with, for example, palladium acetate and carbon monoxide in the presence of an inorganic base at elevated temperature and pressure in a solvent such as dimethyl formamide (DMF). Compound 6 may be converted to compound 7 by treatment of 6 with ammonia or ammonium hydroxide solution. Compound 8 may be obtained by treatment of 7 with a coupling reagent, for example HATU, in the presence of, for example, 1,2-diamino-nitrobenzene or optionally substituted 1,2-diamino aromatics. Compound 9 may be obtained by treatment of 8 in an acidic media, for example, acetic acid at elevated temperature. Nitro reduction of 9 may be achieved by, for example, palladium catalyzed hydrogenation, to furnish compound 10.

Compounds of the present invention (e.g., L=—N(R)S(O)$_2$—; —N(R)C(O)N(H)—; —N(R)C(O)—) may be obtained by treatment of 10 with acid chloride, sulfonyl chloride, isocyanate, or subjecting 10 under reductive alkylation condition with aldehyde or ketone, or coupling conditions with carboxylic acid. Protocols for all such chemical treatment and conversions are well established and are familiar to those skilled in the art. The reagents used in these procedures may have their reactive functional group attached directly to an aromatic moiety, or indirectly through a C1 to C3 saturated or unsaturated carbon chain, or may be attached to a non-aromatic moiety. In cases where an aromatic moiety is part of these reagents, the aromatic moiety may be a five or six membered rings, with one or more substituents of halogen, lower alkyls, lower alkoxyls, additionally substituted or unsubstituted aryls. This aromatic moiety may also be fused with other aromatic ring structures. In cases where these reagents are not readily commercially available, the reagents may be prepared using protocols well established in the field, or the compounds of the present invention may be specifically synthesized using alternative methods familiar to those practice in the field, for example by converting 10 to its phenyl carbamate, and subsequently converting the carbamate into ureas.

Alternatively, compounds of the present invention may be readily prepared according to scheme 2, wherein compound 11, wherein L and R$^3$ are as defined for the compound of formula 1, prepared according to procedures familiar to those skilled in the art, may be subjected to coupling conditions using, for example, HATU in the presence of compound 7 to furnish compound 12, Compound 12 may be treated in an acidic media, for example, acetic acid, to generate the compounds of the present invention.

Scheme 2

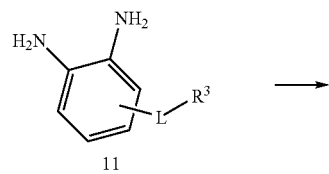

11

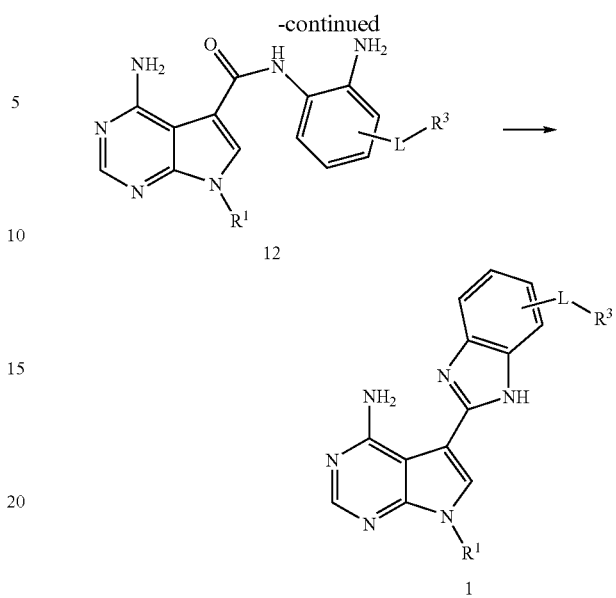

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the later back to the free base compound by treatment with an alkaline reagent and subsequently convert the latter free base to a pharmaceutically acceptable acid addition salt. The acid addition salt of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those, which form non-toxic, base salts with the acidic compounds of formula 1, Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are inhibitors/antagonists of various enzymes/receptors. They are active against a variety of kinase targets which are involved in angiogenesis/vasculogenesis, oncogenic and protooncogenic signal transduction and cell cycle regulations. As such, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant ligand/receptor expression, interaction, activation or signal events related to various protein kinases, are involved. Such disorders may include those of neuronal, glial, astrocytal, hypothalamic, and other glandular macrophagal, epithelia, stromal, and blastocoelic naturein which aberrant function, expression, activation or signaling of a protein kinase are involved. In addition, the compounds of the present invention may have therapeutic utility in inflammatory, angiogenic and immunologic disorders involving both identified and as yet unidentified kinases that are inhibited by the compounds of this invention.

The compounds of the present invention may also be useful in the treatment of additional disorders in which aberrant expression ligand/receptor interactions or activation or signaling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signaling of tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The compounds of the present invention have been found to be selective inhibitors of the tyrosine kinase Tie-2 and related family members. The potency of the compounds of the present invention at the tyrosine kinases may be determined using the following assays.

The in vitro activity of the compounds of formula 1 in inhibiting the Tie-2 receptor may be determined by the following procedure.

Inhibition of Tie-2 tyrosine kinase activity was measured in 96-well Maxisorp plates (Nunc) coated with poly-Glu-Tyr (PGT 4:1, Sigma) by the addition of 100 µL/well of a 25 µg/mL solution of PGT in PBS. Plates were incubated at 37° C. overnight, and transferred to 4° C. until use. Prior to compound testing, appropriate dilutions of compounds were made in 96-well polypropylene plates. The compounds were diluted to 60-fold the desired final concentrations in DMSO, and subsequently diluted to 4-fold the desired final concentrations in phosphorylation buffer-DTT (PB-DTT), a buffer composed of 50 mM HEPES, pH 7.4, 125 mM NaCl, 24 mM $MgCl_2$, and 2 mM of freshly added dithiothreitol (DTT; Sigma). The PGT-coated plates were removed from 4° C., and washed 5 times with TBST, a wash buffer composed of 1× Tris-buffered saline made from powder (Sigma) containing 0.1% polyoxyethylenesorbitan monolaurate (Tween-20, Sigma). Twenty-five µL of each compound dilution per well was added to the washed PGT-coated plate. Plates then received 50 µL/well of a solution of 200 mM ATP (Sigma), freshly diluted in PB-DTT from a frozen 50 mM stock solution. Control wells received 50 µL/well PB-DTT lacking ATP. Reactions were initiated by the addition of 25 µL of purified GST-Tie2 fusion protein in PB-DTT. GST-Tie2 was previously isolated from insect cells infected with GST-Tie2 baculoviruses, and used at concentrations determined to provide $OD_{450}$ signals of approximately 1.0 in the presence of ATP and the absence of chemical inhibitors. Reactions were allowed to proceed for 15 minutes at ambient temperatures with shaking, and terminated by washing 5 times with TBST. To detect phosphotyrosine, the wash buffer was removed, and each well received 75 µL of a horseradish peroxidase-conjugated monoclonal antibody to phosphotyrosine (HRP-PY20; Signal Transduction Labs), diluted 1:2000 in block buffer, a buffer composed of wash buffer and 5% bovine serum albumin (BSA: Sigma). Plates were incubated for 30 minutes with shaking at ambient temperature, and washed 5 times with wash buffer. The bound HRP-PY20 antibody was detected by the addition of 70 µL/well TMB microwell substrate (KPL), and color development was terminated by the addition of an equal volume of 0.9 M $H_2SO_4$. The background signal from wells lacking ATP was subtracted from all ATP-stimulated wells, and $IC_{50}$ values were calculated.

The cell assay utilized NIH/3T3 fibroblasts expressing a chimeric receptor composed of the extra cellular domain of the human EGFR, and the intracellular domain of human Tie-2. To measure cellular activity, fifteen thousand cells were seeded into 96-well U-bottom plates (Falcon) in Dulbecco's Modified Essential Medium (DMEM) containing 2 mM L-glutamine, 0.1 U/mL penicillin, 0.1 µg/mL streptomycin and 10% fetal calf serum (FCS; all supplements from Gibco). Cells were allowed to attach for six hours at 37° C., 5% $CO_2$, at which time the medium was replaced with 190 µL/well starvation medium (fresh medium containing 0.1% FCS). The cell plates were returned to the incubator until the next day. Prior to compound testing, appropriate dilutions of compounds were made in 96-well polypropylene plates. The initial dilution series began with the addition of 15 µL of a 4 mM compound stock solution in DMSO to 45 µL DMSO; the resulting concentration of 1 mM was diluted in a serial 1:4 fashion in DMSO to give concentrations of 1000, 250, 62.5, 15.63, 3.91, 0.98, 0.25 and 0 µM. In a separate 96-well plate, 20 µL of each compound dilution was then added to 80 µL of starvation medium to give compound concentrations of 200, 50, 12.5, 3.13, 0.78, 0.20, 0.049 and 0 µM in a final DMSO concentration of 20%. To dose cells, 10 µL of the various compound dilutions were added to the plates containing cells, to give final compound concentrations of 10, 2.5, 0.63, 0.16, 0.039, 0.01, 0.002 and 0 µM in 1% DMSO. Cell plates were allowed to incubate with compounds for 60 minutes at 37° C., 5% $CO_2$. To activate the chimeric receptors, recombinant EGF (Sigma) was added to a final concentration of 200 ng/mL, and plates were incubated for an additional 10 minutes at 37° C., 5% $CO_2$. Medium was then removed, and the cells were fixed for 5 minutes on ice with 100 µL/well cold methanol containing 200 µM $NaVO_4$. The fixative was removed and plates were allowed to dry at ambient temperature. Phosphotyrosine levels were measured in a time-resolved immunoassay with DELFIA Eu-N[1] -labeled Anti-Phosphotyrosine Antibody (PT66) from Perkin Elmer™. The antibody was diluted to a final concentration of 0.5 µg/mL in DELFIA Assay Buffer (Perkin Elmer™), and 100 µL/well was added for 60 minutes at ambient temperature with shaking. The antibody solution was removed, and plates were washed six times using 300 µL/well DELFIA Wash Buffer (Perkin Elmer™). After the final wash, 100 µL/well of DELFIA Enhancement Solution (Perkin Elmer™) was added to each well. The DELFIA Enhancement Solution (Perkin Elmer™) acts to dissociate the Europium ions, which form highly fluorescent chelates. After incubation at ambient temperatures for 5 minutes with shaking, the plates are read on a Victor 2 Multilabel HTS Counter (Perkin Elmer™). The background signal from mock-stimulated wells is subtracted from the EGF-stimulated wells, and $IC_{50}$ values are calculated.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumor substances, for example those selected from, for example, mitotic inhibitors, for example vinblastine; alkylating agents, for example cicplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-(N-(3,4-dihydro-2-methyl-4-oxoquinazolin-6-ylmethyl)-N-methylamino]-2-thenoyl)-L-glutamic acid; growth factor inhibitor; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-trifluoromethyl) propionanilide). Such conjoint treatment may be achieved by way of simultaneous, sequential or separate dosing of the individual components of the treatment.

The pharmaceutical composition may, for example, be in a form suitable for oral administration as a tablet, capsule, pill, powder, sustained release formulations, solution, and suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled n this art. For example, see Remington's Pharmaceutical Sciences, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

Detailed analytical and preparative HPLC chromatography methods referred to in the preparations and examples below are outlined as follows.

Analytical HPLC method 1. 2. 3 and 4: Gilson HPLC equipped with a diode array detector and a MetaChem Polaris 5 um C18-A 20×2.0 mm column; peak detection reported usually in total intensity chromatogram and 210 nm wavelength; solvent A: water with 2% acetonitrile and 0.01% formic acid, solvent B: acetonitrile with 0.05% formic acid; flow rate at 1 mL/min.

Method 1 gradient: 5% to 20% solvent B in 1 min., ramp up to 100% solvent B at 2.25 min., stay at 100% B until 2.5 min., and back to 5% B at 3.75 min.

Method 2 gradient: 5% to 20% solvent B in 1.25 min., ramp up to 50% at 2.5 min., and up to 100% B at 3.25 min., stay at 100% B until 4.25 min., and back to 5% B at 4.5 min.

Method 3 gradient: stay at 0% solvent B until 1.0 min., ramp up to 20% at 2.0 min., up, to 100% B at 3.5 min., back to 0% B at 3.75 min.

Method 4 gradient: 5% to 20% solvent B in 1.05 min., ramp up to 50% at 4.0 min., and up to 100% B at 4.5 min., back to 5% B at 5.5 min. and stayed at 5% B until 5.75 min.

Analytical HPLC method 5: Hewlett Packard-1050 equipped with a diode array detector and a 150×4 mm Hewlett Packard ODS Hypersil column; peak detection reported at 254 and 300 nm wavelength; solvent A: water with ammonium acetate/acetic acid buffer (0.2 M), solvent B: acetonitrile; flow rate at 3 mL/min.

Method 5 gradient: 0% to 100% B in 10 min., hold at 100% B for 1.5 min.

Preparative HPLC method: Shimadzu HPLC equipped with a diode array detector and a Waters Symmetry or Xterra C8 column, 19×50 mm, 30×50 mm or 50×50 mm; peak detection reported usually at 210 nm wavelength; solvent A: water with 2% acetonitrile and 0.1% formic acid, solvent B: acetonitrile with 0.1% formic acid; flow rate between 18 to 40 mL/min.

General preparative HPLC gradient methods are usually a linear 0 to 5% B to 100% B over 10 to 25 min. Special gradient methods with a narrower gradient window, customized using methods familiar to those skilled in the art, are used for some compounds.

EXAMPLE 1

1A.
4-Chloro-7-cyclopentyl-7H-pyrrolo[2,3-d]pyrimidine

NaH (3.8 g, 95.3 mmol) was added to a solution of 4-Chloro-7H-pyrrolo[2,3-d]pyrimidine (10 g, 63.5 mmol) in DMF (50 mL) at 0° C. The resulting mixture was stirred at 0° C. for 30 min, then warmed to room temperature. At this time Cyclopentylbromide (18.9 g, 127 mmol) was added and the reaction was heated to 60° C. After 4 h the reaction was cooled to 0° C. and quenched slowly with water. The aqueous layer was extracted with EtOAc (3×), the combined organic layers were washed with water (1×), dried over $Na_2SO_4$, and concentrated. Purification by flash column chromatography (Hexanes/Ethyl acetate 9:1) afforded the title compound (10.6 g, 75%). MS: 222.1/224.1 (MH+); retention time 5.77 min. (HPLC method 4).

Similar alkylation procedures were also employed using $Cs_2CO_3$ or $K_2CO_3$ as the base, or using the Mitsunobu condition.

1B. 5-Iodo-4-chloro-7-cyclopentyl-7H-pyrrolo[2,3-d]pyrimidine

To a stirred solution of 4-Chloro-7-cyclopentyl-7H-pyrrolo[2,3-d]pyrimidine (1A, 116 g, 0.52 mole) in 1200 mL CH2CL2 was slowly added a dark brown solution of iodine monochloride (1.0 M, 785 mL) at room temperature over 30 minutes. The reaction mixture was refluxed for 22 h, cooled to room temperature and concentrated. The residue was redissolved in EtOAc, washed with saturated Na2SO3, H2O and brine. The organic layer was dried over Na2SO4 and concentrated. The residue was then recrystalized from i-PrOH to furnish 95 g white crystalline product.

1C. 4-Chloro-7-cyclopentyl-7H-pyrrolo[2,3-d]pyrimidine-5-carboxylic acid

Starting material (1B, 10 g, 29 mmole) was taken in 500 mL DMF and 100 mL H2O together with palladium acetate (0.32 g, 1.4 mmole). The reaction mixture was stirred in a pressure reactor at 50° C. under 100 psi carbon monoxide for 6.5 h and room temperature for 16 h. The reaction mixture was then concentrated and residue triturated with 100 mL of 1:1 EtOAc/Ch2Cl2 followed by 50 mL CH2Cl2, The solid was collected after filtration and dried over P2O5 to furnish 21 g of an off-white solid. This solid was then triturated with a mixture of formic acid/H2O (21 mL/5 mL). The solid collected after filtration and drying over P2O5 furnished 6.5 g of 1 C (m/z 265.1, retention time 2.5 min. with HPLC method 1).

1D. 4-Amino-7-cyclopentyl-7H-pyrrolo[2,3-d]pyrimidine-5-carboxylic acid

The starting material (1 C, 2.0 g, 7.5 mmol) was treated with 30 mL of concentrated ammonium hydroxide in 60 mL of dioxane at 120° C. for 16 h. LCMS monitor suggested reaction completed. The mixture was concentrated and dried under high vacuum to furnish 1.9 g of 1D (m/z 246.2, retention time 2.1 min. with HPLC method 1).

1E. 7-Cyclopentyl-5-(6-nitro-1H-benzoimidazol-2-yl)-7H-pyrrolo[2,3-d]pyrimidin-4-ylamine 4-Amino-7-cyclopentyl-7H-pyrrolo[2,3-d]pyrimidine-5-carboxylic acid (ID, 12.0 g, 488 mmol), 1,2-diamino-4-nitrobenzene (11.2 g, 73.1 mmol), and HATU (26.0 g, 73.1 mmol) were combined and stirred in 242 mL of anhydrous NMP under $N_2$ at 50° C. After 6 hrs, reaction was monitored by LCMS confirming the loss of the starting material and the formation of a new component. The reaction mixture was decant into ten 50 mL centrifuge tubes and concentrated overnight in the GeneVac. Dark brown oil was taken up in EtOAc (1.6 L) and extracted using 1.2 L $H_2O$. The organic layer was washed with $H_2O$ (3×900 mL) and then concentrated. The residue (dark brown gum) was triturate in ~900 mL $CH_2Cl_2$, 10.02 g of a reddish black solid was collected after filtration and vacuum drying. $^1H$ NMR suggested it contained the coupling product plus 20-30% impurity. The solid was again taken up in 1.5 L EtOAc, washed with $H_2O$ (5×900 mL). The organic layer was concentrated and residue triturated in ~900 mL $CH_2Cl_2$, filtered and dried to furnish 7.65 g of a yellow solid. $^1H$ NMR and LCMS suggested the coupling product plus minor impurities (88% pure by LCMS at 210 nm, M/Z 381.5, retention time 2.3 min. with analytical HPLC method 1).

The coupling product was usually cyclized in acidic media, acetic acid or hydrochloric acid or a combination of both, at an elevated temperature of 95° C. The crude product, after removal of the acids via concentration, was taken into the reduction without further purification.

1F. 5-(6-Amino-1H-benzoimidazol-2-yl)-7-cyclopentyl-7H-pyrrolo[2,3-d]pyrimidin-4-ylamine 7-Cyclopentyl-5-(6-nitro-1H-benzoimidazol-2-yl)-7H-pyrrolo[2,3-d]pyrimidin-4-ylamine (1E, 1.0 g) was combined with 10% Palladium on carbon (100 mg) in 50 mL of anhydrous NMP and subjected to 50 psi of hydrogen at room temperature for 24 hours. LCMS monitor suggested pure desired product (M/Z 333.5, retention time 0.70 min. with analytical HPLC method 4). The mixture was filtered through celite. Desired product was used as an NMP stock solution (concentration of about 0.92 g in 45 mL).

EXAMPLE 2

N-[2-(4-Amino-7-cyclopentyl-7H-pyrrolo[2,3-d]pyrimidin-5-yl)-3H-benzoimidazol-5-yl]-3-fluoro-benzenesulfonamide The title compound was prepared by treatment of 5-(6-Amino-1H-benzoimidazol-2-yl)-7-cyclopentyl-7H-pyrrolo[2,3-d]pyrimidin-4-ylamine (1E, 20 mg in 1.0 mL NMP) with 1.2 equiv. of 3-fluoro-benzenesulfonyl chloride (14.3 mg) at 80° C. for 2.5 h. LCMS was used to confirm product formation and the resulting reaction mixture was diluted with 1.0 mL DMSO and purified via preparative HPLC to furnish the desired product (M/Z 491.2, retention time 2.3 min. with analytical HPLC method 2).

EXAMPLE 3

1-[2-(4-Amino-7-cyclopentyl-7H-pyrrolo[2,3-d]pyrimidin-5-yl)-3H-benzoimidazol-5-yl]-3-phenyl-urea The title compound was prepared by treatment of 5-(6-Amino-1H-benzoimidazol-2-yl)-7-cyclopentyl-7H-pyrrolo[2,3-d]pyrimidin-4-ylamine (1E, 20 mg in 1.0 mL NMP) with 1.2 equiv. of phenyl isocyanate (8.7 mg) at 80° C. for 2.5 h. LCMS was used to confirm product formation and the resulting reaction mixture was diluted with 1.0 mL DMSO and purified via preparative HPLC to furnish the desired product (M/Z 452.4, retention time 2.2 min. with analytical HPLC method 2).

EXAMPLES 4-39

Examples 4-39 listed in the following table were prepared using procedures analogous to those described in Examples 1, 2, and 3.

| Example | Compound Name | M/Z | HPLC RT (min) | method |
|---|---|---|---|---|
| 4 | N-[2-(4-Amino-7-cyclopentyl-7H-pyrrolo[2,3-d]pyrimidin-5-yl)-1H-benzoimidazol-5-yl]-2,6-difluoro-benzenesulfonamide | 509.1 | 1.2 | 2 |
| 5 | N-[2-(4-Amino-7-cyclopentyl-7H-pyrrolo[2,3-d]pyrimidin-5-yl)-3H-benzoimidazol-5-yl]-2,4-difluoro-benzenesulfonamide | 509.1 | 2.6 | 1 |
| 6 | 5-(6-Amino-1H-benzoimidazol-2-yl)-7-cyclopentyl-7H-pyrrolo[2,3-d]pyrimidin-4-ylamine | 333.5 | 0.7 | 2 |
| 7 | 1-[2-(4-Amino-7-cyclopentyl-7H-pyrrolo[2,3-d]pyrimidin-5-yl)-3H-benzoimidazol-5-yl]-3-p-tolyl-urea | 466.4 | 2.6 | 2 |
| 8 | 1-[2-(4-Amino-7-cyclopentyl-7H-pyrrolo[2,3-d]pyrimidin-5-yl)-3H-benzoimidazol-5-yl]-3-m-tolyl-urea | 466.4 | 2.6 | 2 |
| 9 | 1-[2-(4-Amino-7-cyclopentyl-7H-pyrrolo[2,3-d]pyrimidin-5-yl)-3H-benzoimidazol-5-yl]-3-(2-fluoro-phenyl)-urea | 470.4 | 2.4 | 2 |
| 10 | 1-[2-(4-Amino-7-cyclopentyl-7H-pyrrolo[2,3-d]pyrimidin-5-yl)-3H-benzoimidazol-5-yl]-3-(3-ethyl-phenyl)-urea | 480.4 | 2.8 | 2 |
| 11 | 1-[2-(4-Amino-7-cyclopentyl-7H-pyrrolo[2,3-d]pyrimidin-5-yl)-3H-benzoimidazol-5-yl]-3-(2-methoxy-phenyl)-urea | 481.9 | 2.6 | 2 |
| 12 | 1-[2-(4-Amino-7-cyclopentyl-7H-pyrrolo[2,3-d]pyrimidin-5-yl)-3H-benzoimidazol-5-yl]-3-(3-methoxy-phenyl)-urea | 482.0 | 2.4 | 2 |
| 13 | 1-[2-(4-Amino-7-cyclopentyl-7H-pyrrolo[2,3-d]pyrimidin-5-yl)-3H-benzoimidazol-5-yl]-3-(4-methoxy-phenyl)-urea | 482.4 | 2.1 | 2 |
| 14 | 1-[2-(4-Amino-7-cyclopentyl-7H-pyrrolo[2,3-d]pyrimidin-5-yl)-3H-benzoimidazol-5-yl]-3-(2-fluoro-5-methyl-phenyl)-urea | 484.4 | 2.6 | 2 |
| 15 | 1-[2-(4-Amino-7-cyclopentyl-7H-pyrrolo[2,3-d]pyrimidin-5-yl)-3H-benzoimidazol-5-yl]-3-(2-chloro-phenyl)-urea | 486.3 | 2.6 | 2 |
| 16 | 1-[2-(4-Amino-7-cyclopentyl-7H-pyrrolo[2,3-d]pyrimidin-5-yl)-3H-benzoimidazol-5-yl]-3-(4-chloro-phenyl)-urea | 486.3 | 2.8 | 2 |
| 17 | 1-[2-(4-Amino-7-cyclopentyl-7H-pyrrolo[2,3-d]pyrimidin-5-yl)-3H-benzoimidazol-5-yl]-3-(3,5-difluoro-phenyl)-urea | 488.4 | 2.7 | 2 |
| 18 | 1-[2-(4-Amino-7-cyclopentyl-7H-pyrrolo[2,3-d]pyrimidin-5-yl)-3H-benzoimidazol-5-yl]-3-(3,4-difluoro-phenyl)-urea | 488.4 | 2.6 | 2 |

-continued

| Example | Compound Name | M/Z | HPLC RT (min) | method |
|---|---|---|---|---|
| 19 | 1-[2-(4-Amino-7-cyclopentyl-7H-pyrrolo[2,3-d]pyrimidin-5-yl)-3H-benzoimidazol-5-yl]-3-(2,5-difluoro-phenyl)-urea | 488.4 | 2.8 | 2 |
| 20 | 1-[2-(4-Amino-7-cyclopentyl-7H-pyrrolo[2,3-d]pyrimidin-5-yl)-3H-benzoimidazol-5-yl]-3-(2,6-difluoro-phenyl)-urea | 488.3 | 2.1 | 2 |
| 21 | 1-[2-(4-Amino-7-cyclopentyl-7H-pyrrolo[2,3-d]pyrimidin-5-yl)-3H-benzoimidazol-5-yl]-3-(2,4-difluoro-phenyl)-urea | 488.4 | 2.5 | 2 |
| 22 | 1-[2-(4-Amino-7-cyclopentyl-7H-pyrrolo[2,3-d]pyrimidin-5-yl)-3H-benzoimidazol-5-yl]-3-(2-methoxy-5-methyl-phenyl)-urea | 496.4 | 2.7 | 2 |
| 23 | 1-[2-(4-Amino-7-cyclopentyl-7H-pyrrolo[2,3-d]pyrimidin-5-yl)-3H-benzoimidazol-5-yl]-3-(2-ethoxy-phenyl)-urea | 496.4 | 2.7 | 2 |
| 24 | N-[2-(4-Amino-7-cyclopentyl-7H-pyrrolo[2,3-d]pyrimidin-5-yl)-3H-benzoimidazol-5-yl]-4-ethyl-benzenesulfonamide | 501.4 | 2.6 | 2 |
| 25 | N-[2-(4-Amino-7-cyclopentyl-7H-pyrrolo[2,3-d]pyrimidin-5-yl)-3H-benzoimidazol-5-yl]-4-methoxy-benzenesulfonamide | 503.2 | 2.2 | 2 |
| 26 | N-[2-(4-Amino-7-cyclopentyl-7H-pyrrolo[2,3-d]pyrimidin-5-yl)-3H-benzoimidazol-5-yl]-4-chloro-benzenesulfonamide | 507.3 | 2.6 | 2 |
| 27 | N-[2-(4-Amino-7-cyclopentyl-7H-pyrrolo[2,3-d]pyrimidin-5-yl)-3H-benzoimidazol-5-yl]-2-chloro-benzenesulfonamide | 507.3 | 2.3 | 2 |
| 28 | N-[2-(4-Amino-7-cyclopentyl-7H-pyrrolo[2,3-d]pyrimidin-5-yl)-3H-benzoimidazol-5-yl]-2,5-difluoro-benzenesulfonamide | 509.3 | 2.3 | 2 |
| 29 | N-[2-(4-Amino-7-cyclopentyl-7H-pyrrolo[2,3-d]pyrimidin-5-yl)-3H-benzoimidazol-5-yl]-3,4-difluoro-benzenesulfonamide | 509.4 | 2.5 | 2 |
| 30 | N-[2-(4-Amino-7-cyclopentyl-7H-pyrrolo[2,3-d]pyrimidin-5-yl)-3H-benzoimidazol-5-yl]-2-methoxy-4-methyl-benzenesulfonamide | 517.4 | 2.3 | 2 |
| 31 | N-[2-(4-Amino-7-cyclopentyl-7H-pyrrolo[2,3-d]pyrimidin-5-yl)-3H-benzoimidazol-5-yl]-3-chloro-2-methyl-benzenesulfonamide | 521.3 | 2.8 | 2 |
| 32 | N-[2-(4-Amino-7-cyclopentyl-7H-pyrrolo[2,3-d]pyrimidin-5-yl)-3H-benzoimidazol-5-yl]-3-chloro-4-methyl-benzenesulfonamide | 521.1 | 2.8 | 2 |
| 33 | N-[2-(4-Amino-7-cyclopentyl-7H-pyrrolo[2,3-d]pyrimidin-5-yl)-3H-benzoimidazol-5-yl]-3-chloro-4-fluoro-benzenesulfonamide | 525.3 | 2.2 | 2 |
| 34 | N-[2-(4-Amino-7-cyclopentyl-7H-pyrrolo[2,3-d]pyrimidin-5-yl)-3H-benzoimidazol-5-yl]-5-chloro-2-methoxy-benzenesulfonamide | 537.2 | 2.5 | 2 |
| 35 | N-[2-(4-Amino-7-cyclopentyl-7H-pyrrolo[2,3-d]pyrimidin-5-yl)-3H-benzoimidazol-5-yl]-3,5-dichloro-benzenesulfonamide | 541.3 | 3.0 | 2 |
| 36 | N-[2-(4-Amino-7-cyclopentyl-7H-pyrrolo[2,3-d]pyrimidin-5-yl)-3H-benzoimidazol-5-yl]-2,4-dichloro-benzenesulfonamide | 541.2 | 2.8 | 2 |
| 37 | Biphenyl-3-sulfonic acid [2-(4-amino-7-cyclopentyl-7H-pyrrolo[2,3-d]pyrimidin-5-yl)-3H-benzoimidazol-5-yl]-amide | 549.4 | 2.9 | 2 |
| 38 | N-[2-(4-Amino-7-cyclopentyl-7H-pyrrolo[2,3-d]pyrimidin-5-yl)-3H-benzoimidazol-5-yl]-2-trifluoromethoxy-benzenesulfonamide | 557.3 | 2.7 | 2 |
| 39 | N-[2-(4-Amino-7-cyclopentyl-7H-pyrrolo[2,3-d]pyrimidin-5-yl)-3H-benzoimidazol-5-yl]-3-(pyridin-2-yloxy)-benzenesulfonamide | 566.3 | 2.5 | 2 |

What is claimed is:

1. A compound of the formula 1

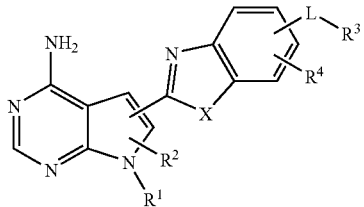

or a pharmaceutically acceptable salt thereof, wherein:

X is HN, $(C_1-C_6)$alkyl-N, $(C_3-C_8)$cycloalkyl-N, O or S;

L is —$(CH_2)_p$—, wherein p is an integer from 0 to 5; —O—; —S—; —S(O)—; —S(O)$_2$; —N(R)—; —N(C(O)OR)—; —N(C(O)R)—; —N(S(O)$_2$R)—; —CH$_2$O—; —CH$_2$S—; —CH$_2$N(R)—; —C(=NR)—; —CH$_2$(N(C(O)R)—; —CH$_2$N(C(O)OR)—; —CH$_2$N(S(O)$_2$R)—; —CH(NHR)—; —CH(NHC(O)R)—; —CH(NHS(O)$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; —OC(O)N(R)—; —N(R)C(O)N(R)—; —N(R)C(O)O—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —S(O)N(C(O)R)—; —S(O)$_2$N(C(O)R)—; —C(O)O—; —N(R)P(OR$^5$)O—; —N(R)P(OR$^5$)—; —N(R)P(O)(OR$^5$)O—; —N(R)P(O)(OR$^5$)—; —N(C(O)R)P(OR$^5$)O—; —N(C(O)R)P(OR$^5$)—; —N(C(O)R)P(O)(OR$^5$)O—; —CH(R)S(O)—; —CH(R)S(O)$_2$—; —CH(R)N(C(O)OR$^5$)—; —CH(R)N(C(O)R)—; —CH(R)N(SO$_2$R)—; —CH(R)O—; —CH(R)S—; —CH(R)N(R)—; —CH(R)N(C(O)R)—; —CH(R)N(C(O)OR)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; —CH(R)N(R)S(O)$_2$—; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; —CH(R)N(R)S(O)O—; —CH(R)N(R)S(O)$_2$O—; —CH(R)N(R)S(O)C(O)—; —CH(R)N(R)S(O)$_2$C(O)—; —CH(R)S(O)N(C(O)R)—; —CH(R)S(O)$_2$N(C(O)R)—; —CH(R)N(R)S(O)N(R)—; —CH(R)N(R)S(O)$_2$N(R)—; —CH(R)C(O)O—; —CH(R)N(R)P(OR$^5$)O—; —CH(R)N(R)P(OR$^5$)—; —CH(R)N(R)P(O)(OR$^5$)O—; —CH(R)N(R)P(O)(OR$^5$)—; —CH(R)N(C(O)R)P(OR$^5$)O—; —CH(R)N(C(O)R)P(OR$^5$)—; —CH(R)N(C(O)R)P(O)(OR$^5$)O— or —CH(R)N(C(O)R)P(OR$^5$)—; wherein each R is independently selected from the group consisting of H, $(C_1-C_6)$alkylcarbonyl, $(C_1-C_6)$alkyl, $(C_6-C_{10})$aryl and $(C_1-C_{10})$heteroaryl; wherein each of the aforesaid $(C_1-C_6)$alkylcarbonyl, $(C_1-C_6)$alkyl, $(C_6-C_{10})$aryl, and $(C_1-C_{10})$heteroaryl groups is independently optionally substituted with 1-3 substituents independently selected from halogen, $(C_1-C_6)$alkyl and $(C_1-C_6)$alkoxy;

$R^1$ is H, $(C_1-C_6)$alkyl, $(C_3-C_8)$cycloalkyl, $(C_6-C_{10})$aryl, $(C_1-C_{10})$heteroaryl, or $(C_3-C_8)$heterocycloalkyl, wherein each of the aforesaid $(C_1-C_6)$alkyl, $(C_3-C_8)$cycloalkyl, $(C_6-C_{10})$aryl, $(C_1-C_{10})$heteroaryl, and $(C_3-C_8)$heterocycloalkyl groups is optionally independently substituted with 1 to 5 $(C_1-C_6)$alkyl groups;

$R^2$ is H, halo, $(C_1-C_6)$alkyl, $(C_3-C_8)$cycloalkyl, $(C_6-C_{10})$aryl, $(C_1-C_{10})$heteroaryl, $(C_3-C_8)$heterocycloalkyl, —$(CR^{10}R^{11})_n NR^6R^7$ or —$(CR^{10}R^{11})_n C(O)NR^6R^7$; wherein n is an integer from 0-3; and each of the aforesaid $(C_1-C_6)$alkyl, $(C_3-C_8)$cycloalkyl, $(C_6-C_{10})$aryl, $(C_1$- $(C_3-C_8)$heterocycloalkyl groups is optionally independently substituted with 1 to 5 $R^8$ substituents;

$R^3$ is H, $(C_1-C_6)$alkyl, $(C_3-C_8)$cycloalkyl, —$(CR^{10}R^{11})_t(C_6-C_{10})$aryl, —$(CR^{10}R^{11})_t(C_1-C_{10})$heteroaryl, or $(C_3-C_8)$heterocycloalkyl; and each of the aforesaid $(C_1-C_6)$alkyl, $(C_3-C_8)$cycloalkyl, —$(CR^{10}R^{11})_t(C_6-C_{10})$aryl, —$(CR^{10}R^{11})_t(C_1-C_{10})$heteroaryl, and $(C_3-C_8)$heterocycloalkyl groups is optionally independently substituted with 1 to 5 $R^{12}$ groups;

$R^4$ is H, halo, $(C_1-C_6)$alkyl, $(C_3-C_6)$cycloalkyl, $(C_1-C_6)$alkoxy, or $(C_3-C_6)$cycloalkoxy;

each $R^5$ is H, $(C_1-C_6)$alkylcarbonyl, $(C_1-C_6)$alkyl, $(C_6-C_{10})$aryl or $(C_1-C_{10})$heteroaryl; wherein each of the aforesaid $(C_1-C_6)$alkylcarbonyl, $(C_1-C_6)$alkyl, $(C_6-C_{10})$aryl, and $(C_1-C_{10})$heteroaryl groups is independently optionally substituted with 1-3 substituents independently selected from halogen, $(C_1-C_6)$alkyl and $(C_1-C_6)$alkoxy;

each $R^6$ and $R^7$ is independently H, $(C_1-C_6)$alkyl, —$(CR^{10}R^{11})_t(C_6-C_{10})$aryl, —$(CR^{10}R^{11})_t(C_1-C_{10})$heterocyclic, —$(CR^{10}R^{11})_t O(CR^{10}R^{11})_q OR^{10}$, or —$(CR^{10}R^{11})_t OR^{10}$, or $R^6$ and $R^7$ taken together on the same $R^8$ or on the same $R^{12}$ can form a heteroaryl or a heterocycloalkyl group; the $(C_1-C_6)$alkyl, $(C_6-C_{10})$aryl and $(C_1-C_{10})$heterocyclic moieties of the foregoing $R^6$ and $R^7$ groups are optionally substituted by 1 to 3 substituents independently selected from halo, cyano, trifluoromethyl, —$C(O)R^9$, —$NR^{10}C(O)R^{11}$, —$C(O)NR^{10}R^{11}$, —$NR^{10}R^{11}$, $(C_1-C_6)$alkyl, —$(CR^{10}R^{11})_t(C_6-C_{10})$aryl, —$(CR^{10}R^{11})_t(C_1-C_{10})$heterocyclic, —$(CR^{10}R^{11})_t O(CR^{10}R^{11})_q OR^{10}$, and —$(CR^{10}R^{11})_t OR^{10}$; and further that where $R^6$ and $R^7$ are both attached to the same nitrogen, then $R^6$ and $R^7$ are not both bonded to the nitrogen directly through an oxygen;

each $R^8$ and $R^{12}$ is independently halo, cyano, trifluoromethoxy, trifluoromethyl, —$C(O)R^9$, —$NR^6C(O)R^7$, —$C(O)NR^6R^7$, —$NR^6R^7$, —$OR^{10}$, —$SO_2NR^6R^7$, —$SO_2R^6$, —$NR^6SO_2R^7$, $(C_1-C_6)$alkyl, $(C_2-C_6)$alkenyl, $(C_2-C_6)$alkynyl, —$(CR^{10}R^{11})_t O(CR^{10}R^{11})_q NR^6R^7$, —$(CR^{10}R^{11})_t O(CR^{10}R^{11})_q OR^{10}$, —$(CR^{10}R^{11})_t OR^{10}$, —$S(O)_j(C_1-C_6)$alkyl, —$(CR^{10}R^{11})_t(C_6-C_{10})$aryl, —$(CR^{10}R^{11})_t(C_1-C_{10})$heterocyclic, —$(CR^{10}R^{11})_t O (CH_2)_q(C_1-C_{10})$heterocyclic, —$C(O)(CR^{10}R^{11})_t(C_1-C_{10})$heterocyclic, —$(CR^{10}R^{11})_t NR^7(CR^{10}R^{11})_q NR^6R^7$, —$(CR^{10}R^{11})_t NR^7 CR^{10}R^{11}C(O)NR^6R^7$, —$(CR^{10}R^{11})_t NR^7(CR^{10}R^{11})_q NR^{10}C(O)R^9$, —$(CR^{10}R^{11})_t NR^7(CR^{10}R^{11})_q O(CR^{10}R^{11})_q OR^{10}$, —$(CR^{10}R^{11})_t NR^7(CR^{10}R^{11})_q S(O)_j(C_1-C_6)$alkyl, —$(CR^{10}R^{11})_t NR^7(CR^{10}R^{11})_q R^6$, —$SO_2(CR^{10}R^{11})_t(C_6-C_{10})$aryl, or —$SO_2(CR^{10}R^{11})_t(C_1-C_{10})$heterocyclic; the —$(CR^{10}R^{11})_q$— and —$(CR^{10}R^{11})_t$— moieties of the foregoing $R^8$ and $R^{12}$ groups optionally include a carbon-carbon double or triple bond; and the $(C_1-C_6)$alkyl, $(C_6-C_{10})$aryl and $(C_1-C_{10})$heterocyclic moieties of the aforesaid $R^8$ and $R^{12}$ groups are optionally substituted on a carbon atom by 1 to 3 substituents independently selected from halo, cyano, trifluoromethyl, —C(O)$R^9$, —NR$^6$C(O)$R^7$, —C(O)NR$^6$R$^7$, —(CR$^{10}$R$^{11}$)$_t$NR$^6$R$^7$, —SO$_2$R$^6$, —SO$_2$NR$^6$R$^7$, $(C_1-C_6)$alkyl, —(CR$^{10}$R$^{11}$)(C$_1$-C$_{10}$)heterocyclic, —(CR$^{10}$R$^{11}$)$_t$O(CR$^{10}$R$^{11}$)$_q$OR$^{10}$, and —(CR$^{10}$R$^{11}$)$_t$OR$^{10}$;

each $R^9$ is independently H, $(C_1-C_{10})$alkyl, —(CR$^{10}$R$^{11}$)$_t$ $(C_6-C_{10})$aryl, or —(CR$^{10}$R$^{11}$)$_t$(C$_1$-C$_{10}$)heterocyclic; and each $R^{10}$ and $R^{11}$ is independently H or $(C_1-C_6)$alkyl;

each j is independently 0, 1 or 2;

each t is independently 0, 1, 2, 3, 4, 5 or 6; and each q is independently 2, 3, 4, 5, or 6.

2. A compound according to claim 1, wherein X is HN, $(C_1-C_6)$alkyl-N—, or $(C_3-C_8)$cycloalkyl-N—.

3. A compound according to claim 2, wherein X is NH.

4. A compound according to claim 2, wherein X is $(C_1-C_6)$alkyl-N— or $(C_3-C_8)$cycloalkyl-N—.

5. A compound according to claim 1, wherein X is O.

6. A compound according to claim 1, wherein X is S.

7. A compound according to claim 1, wherein L is —(CH$_2$)$_p$— wherein p is an integer from 0 to 5; —O—; —S—; —S(O)—; —S(O)2—; —N(R)—; —N(C(O)OR)—; —N(C(O)R)—; —N(S(O)$_2$R)—; —N(R)C(O)—; —N(R)S (O)—; —N(R)S(O)$_2$—; —OC(O)N(R)—; —N(R)C(O)N (R)—; —N(R)C(O)O—; —S(O)N(R)—; —S(O)$_2$N(R)—; —N(C(O)R)S(O)—; —N(C(O)R)S(O)$_2$—; —N(R)S(O)N (R)—; —N(R)S(O)$_2$N(R)—; —C(O)N(R)C(O)—; —S(O)N (R)C(O)—; —S(O)$_2$N(R)C(O)—; —OS(O)N(R)—; —OS (O)$_2$N(R)—; —N(R)S(O)O—; —N(R)S(O)$_2$O—; —N(R)S (O)C(O)—; —N(R)S(O)$_2$C(O)—; —S(O)N(C(O)R)—; —S(O)$_2$N(C(O)R)—; —or —C(O)O—; and wherein each R is independently H, $(C_1-C_6)$alkylcarbonyl, $(C_1-C_6)$alkyl, $(C_6-C_{10})$aryl or $(C_1-C_{10})$heteroaryl, wherein each of the aforementioned $(C_1-C_6)$alkylcarbonyl, $(C_1-C_6)$alkyl, $(C_6-C_{10})$aryl and $(C_1-C_{10})$heteroaryl groups is independently optionally substituted with 1-3 halogens, $(C_1-C_6)$alkyl and $(C_1-C_6)$alkoxy.

8. The compound according to claim 1, wherein L is —O—; —S—; —S(O)$_2$—; —N(R)—; —N(C(O)R)—; —N(S(O)$_2$R); —N(R)C(O)—; —N(R)S(O)$_2$—; —N(R)C (O)N(R)—; —S(O)$_2$N(R)—; —N(C(O)R)S(O)$_2$—; —N(R) S(O)$_2$N(R)—; —C(O)N(R)C(O)—; —S(O)$_2$N(R)C(O)—; —OS(O)$_2$N(R)—; —N(R)S(O)$_2$O—; —N(R)S(O)$_2$C(O)—; —S(O)$_2$N(C(O)R)—; or —C(O)O—; and wherein each R is independently H, $(C_1-C_6)$alkylcarbonyl, $(C_1-C_6)$alkyl, $(C_6-C_{10})$aryl, or $(C_1-C_{10})$heteroaryl, wherein each of the aforementioned $(C_1C_6)$alkylcarbonyl, $(C_1-C_6)$alkyl, $(C_6-C_{10})$aryl, and $(C_1-C_{10})$heteroaryl groups is independently optionally substituted with 1-3 halogens, $(C_1-C_6)$alkyl and $(C_1-C_6)$alkoxy.

9. A compound according to claim 1, wherein L is —N(S (O)$_2$R)— or —N(R)C(O)N(R)— and wherein each R is independently H, $(C_1-C_6)$alkylcarbonyl, $(C_1-C_6)$alkyl, $(C_6-C_{10})$aryl or $(C_1-C_{10})$heteroaryl, wherein each of the aforementioned $(C_1-C_6)$alkylcarbonyl, $(C_1-C_6)$alkyl, $(C_6-C_{10})$aryl, and $(C_1-C_{10})$heteroaryl groups are independently optionally substituted with 1-3 halogens, $(C_1-C_6)$alkyl and $(C_1-C_6)$alkoxy.

10. A compound according to claim 1, wherein L is —N(R) C(O)N(R)— and wherein each R is independently selected from the group consisting of H or $(C_1-C_6)$alkyl.

11. A compound according to claim 1, wherein L is —N(S (O)$_2$R)— and wherein R is selected from the group consisting of H or $(C_1-C_6)$alkyl.

12. A compound according to claim 1, wherein the compound is of formula 2

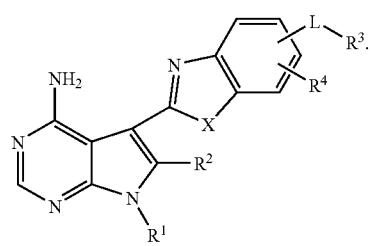

13. A compound according to claim 1, wherein $R^1$ is H, $(C_1-C_6)$alkyl, $(C_3-C_8)$cycloalkyl or $(C_3-C_8)$heterocycloalkyl, wherein each of the aforesaid $(C_1-C_6)$alkyl, $(C_3-C_8)$cycloalkyl, and $(C_3-C_8)$heterocycloalkyl groups is optionally substituted with 1 to 5 $(C_1-C_6)$alkyl groups.

14. A compound according to claim 13, wherein $R^1$ is H, $(C_1-C_6)$alkyl, or $(C_3-C_8)$cycloalkyl, wherein each of the aforesaid $(C_1-C_6)$alkyl and $(C_3-C_8)$cycloalkyl groups is optionally substituted with 1 to 5 $(C_1-C_6)$alkyl groups.

15. A compound according to claim 14, wherein $R^1$ is $(C_1-C_6)$alkyl, or $(C_3-C_8)$cycloalkyl, wherein each of the aforesaid $(C_1-C_6)$alkyl and $(C_3-C_8)$cycloalkyl groups is optionally substituted with 1 to 5 $(C_1-C_6)$alkyl groups.

16. A compound according to claim 14, wherein $R^1$ is $(C_3-C_8)$cycloalkyl which is optionally substituted with 1 to 5 $(C_1-C_6)$alkyl groups.

17. A compound according to claim 1, wherein $R^2$ is H, halo, $(C_1-C_6)$alkyl, $(C_3-C_8)$cycloalkyl, —(CR$^{10}$R$^{11}$)$_n$NR$^6$R$^7$ or —(CR$^{10}$R$^{11}$)$_n$C(O)NR$^6$R$^7$, wherein each of the aforesaid $(C_1-C_6)$alkyl and $(C_3-C_8)$cycloalkyl groups is optionally substituted with 1 to 5 $R^8$ substituents.

18. A compound according to claim 17, wherein $R^2$ is H, halo, or $(C_1-C_6)$alkyl, wherein the $(C_1-C_6)$alkyl group is optionally substituted with 1 to 5 $R^8$ substituents.

19. A compound according to claim 1, wherein $R^3$ is $(C_3-C_8)$cycloalkyl, —(CR$^{10}$R$^{11}$)$_t$(C$_6$-C$_{10}$)aryl, —(CR$^{10}$R$^{11}$)$_t$(C$_1$-C$_{10}$)heteroaryl, or $(C_3-C_8)$heterocycloalkyl, wherein each of the aforesaid $(C_3-C_8)$cycloalkyl, —(CR$^{10}$R$^{11}$)$_t$(C$_6$-C$_{10}$)aryl, —(CR$^{10}$R$^{11}$)$_t$(C$_1$-C$_{10}$)heteroaryl, and $(C_3-C_8)$heterocycloalkyl groups is optionally independently substituted with 1 to 5 $R^{12}$ groups.

20. A compound according to claim 19, wherein $R^3$ is $(C_3-C_8)$cycloalkyl, —(CR$^{10}$R$^{11}$)$_t$(C$_6$-C$_{10}$)aryl, or —(CR$^{10}$R$^{11}$)$_t$(C$_1$-C$_{10}$)heteroaryl, wherein each of the aforesaid $(C_3-C_8)$cycloalkyl, —(CR$^{10}$R$^{11}$)$_t$(C$_6$-C$_{10}$)aryl, and —(CR$^{10}$R$^{11}$)$_t$(C$_1$-C$_{10}$)heteroaryl groups is optionally independently substituted with 1 to 5 $R^{12}$ groups.

21. A compound according to claim 20, wherein $R^3$ is —(CR$^{10}$R$^{11}$)$_t$(C$_6$-C$_{10}$)aryl, or —(CR$^{10}$R$^{11}$)$_t$(C$_1$-C$_{10}$)heteroaryl, wherein each of the aforesaid —(CR$^{10}$R$^{11}$)$_t$(C$_6$-C$_{10}$)aryl, and —(CR$^{10}$R$^{11}$)$_t$(C$_1$-C$_{10}$)heteroaryl groups is optionally independently substituted with 1 to 5 $R^{12}$ groups.

22. A compound according to claim 1, wherein said compound is selected from the group consisting of N-[2-(4-Amino-7-cyclopentyl-7H-pyrrolo[2,3-d]pyrimidin-5-yl)-1H-benzoimidazol-5-yl]-2,6-difluoro-benzenesulfonamide;

N-[2-(4-Amino-7-cyclopentyl-7H-pyrrolo[2,3-d]pyrimidin-5-yl)-3H-benzoimidazol-5-yl]-2,4-difluoro-benzenesulfonamide;
5-(6-Amino-1H-benzoimidazol-2-yl)-7-cyclopentyl-7H-pyrrolo[2,3-d]pyrimidin-4-ylamine;
1-[2-(4-Amino-7-cyclopentyl-7H-pyrrolo[2,3-d]pyrimidin-5-yl)-3H-benzoimidazol-5-yl]-3-p-tolyl-urea;
1-[2-(4-Amino-7-cyclopentyl-7H-pyrrolo[2,3-d]pyrimidin-5-yl)-3H-benzoimidazol-5-yl]-3-m-tolyl-urea;
1-[2-(4-Amino-7-cyclopentyl-7H-pyrrolo[2,3-d]pyrimidin-5-yl)-3H-benzoimidazol-5-yl]-3-(2-fluoro-phenyl)-urea;
1-[2-(4-Amino-7-cyclopentyl-7H-pyrrolo[2,3-d]pyrimidin-5-yl)-3H-benzoimidazol-5-yl]-3-(3-ethyl-phenyl)-urea;
1-[2-(4-Amino-7-cyclopentyl-7H-pyrrolo[2,3-d]pyrimidin-5-yl)-3H-benzoimidazol-5-yl]-3-(2-methoxy-phenyl)-urea;
1-[2-(4-Amino-7-cyclopentyl-7H-pyrrolo[2,3-d]pyrimidin-5-yl)-3H-benzoimidazol-5-yl]-3-(3-methoxy-phenyl)-urea;
1-[2-(4-Amino-7-cyclopentyl-7H-pyrrolo[2,3-d]pyrimidin-5-yl)-3H-benzoimidazol-5-yl]-3-(4-methoxy-phenyl)-urea;
1-[2-(4-Amino-7-cyclopentyl-7H-pyrrolo[2,3-d]pyrimidin-5-yl)-3H-benzoimidazol-5-yl]-3-(2-fluoro-5-methyl-phenyl)-urea;
1-[2-(4-Amino-7-cyclopentyl-7H-pyrrolo[2,3-d]pyrimidin-5-yl)-3H-benzoimidazol-5-yl]-3-(2-chloro-phenyl)-urea;
1-[2-(4-Amino-7-cyclopentyl-7H-pyrrolo[2,3-d]pyrimidin-5-yl)-3H-benzoimidazol-5-yl]-3-(4-chloro-phenyl)-urea;
1-[2-(4-Amino-7-cyclopentyl-7H-pyrrolo[2,3-d]pyrimidin-5-yl)-3H-benzoimidazol-5-yl]-3-(3,5-difluoro-phenyl)-urea;
1-[2-(4-Amino-7-cyclopentyl-7H-pyrrolo[2,3-d]pyrimidin-5-yl)-3H-benzoimidazol-5-yl]-3-(3,4-difluoro-phenyl)-urea;
1-[2-(4-Amino-7-cyclopentyl-7H-pyrrolo[2,3-d]pyrimidin-5-yl)-3H-benzoimidazol-5-yl]-3-(2,5-difluoro-phenyl)-urea;
1-[2-(4-Amino-7-cyclopentyl-7H-pyrrolo[2,3-d]pyrimidin-5-yl)-3H-benzoimidazol-5-yl]-3-(2,6-difluoro-phenyl)-urea;
1-[2-(4-Amino-7-cyclopentyl-7H-pyrrolo[2,3-d]pyrimidin-5-yl)-3H-benzoimidazol-5-yl]-3-(2,4-difluoro-phenyl)-urea;
1-[2-(4-Amino-7-cyclopentyl-7H-pyrrolo[2,3-d]pyrimidin-5-yl)-3H-benzoimidazol-5-yl]-3-(2-methoxy-5-methyl-phenyl)-urea;
1-[2-(4-Amino-7-cyclopentyl-7H-pyrrolo[2,3-d]pyrimidin-5-yl)-3H-benzoimidazol-5-yl]-3-(2-ethoxy-phenyl)-urea;
N-[2-(4-Amino-7-cyclopentyl-7H-pyrrolo[2,3-d]pyrimidin-5-yl)-3H-benzoimidazol-5-yl]-4-ethyl-benzenesulfonamide;
N-[2-(4-Amino-7-cyclopentyl-7H-pyrrolo[2,3-d]pyrimidin-5-yl)-3H-benzoimidazol-5-yl]-4-methoxy-benzenesulfonamide;
N-[2-(4-Amino-7-cyclopentyl-7H-pyrrolo[2,3-d]pyrimidin-5-yl)-3H-benzoimidazol-5-yl]-4-chloro-benzenesulfonamide;
N-[2-(4-Amino-7-cyclopentyl-7H-pyrrolo[2,3-d]pyrimidin-5-yl)-3H-benzoimidazol-5-yl]-2-chloro-benzenesulfonamide;
N-[2-(4-Amino-7-cyclopentyl-7H-pyrrolo[2,3-d]pyrimidin-5-yl)-3H-benzoimidazol-5-yl]-2,5-difluoro-benzenesulfonamide;
N-[2-(4-Amino-7-cyclopentyl-7H-pyrrolo[2,3-d]pyrimidin-5-yl)-3H-benzoimidazol-5-yl]-3,4-difluoro-benzenesulfonamide;
N-[2-(4-Amino-7-cyclopentyl-7H-pyrrolo[2,3-d]pyrimidin-5-yl)-3H-benzoimidazol-5-yl]-2-methoxy-4-methyl-benzenesulfonamide;
N-[2-(4-Amino-7-cyclopentyl-7H-pyrrolo[2,3-d]pyrimidin-5-yl)-3H-benzoimidazol-5-yl]-3-chloro-2-methyl-benzenesulfonamide;
N-[2-(4-Amino-7-cyclopentyl-7H-pyrrolo[2,3-d]pyrimidin-5-yl)-3H-benzoimidazol-5-yl]-3-chloro-4-methyl-benzenesulfonamide;
N-[2-(4-Amino-7-cyclopentyl-7H-pyrrolo[2,3-d]pyrimidin-5-yl)-3H-benzoimidazol-5-yl]-3-chloro-4-fluoro-benzenesulfonamide;
N-[2-(4-Amino-7-cyclopentyl-7H-pyrrolo[2,3-d]pyrimidin-5-yl)-3H-benzoimidazol-5-yl]-5-chloro-2-methoxy-benzenesulfonamide;
N-[2-(4-Amino-7-cyclopentyl-7H-pyrrolo[2,3-d]pyrimidin-5-yl)-3H-benzoimidazol-5-yl]-3,5-dichloro-benzenesulfonamide;
N-[2-(4-Amino-7-cyclopentyl-7H-pyrrolo[2,3-d]pyrimidin-5-yl)-3H-benzoimidazol-5-yl]-2,4-dichloro-benzenesulfonamide;
Biphenyl-3-sulfonic acid [2-(4-amino-7-cyclopentyl-7H-pyrrolo[2,3-d]pyrimidin-5-yl)-3H-benzoimidazol-5-yl]-amide;
N-[2-(4-Amino-7-cyclopentyl-7H-pyrrolo[2,3-d]pyrimidin-5-yl)-3H-benzoimidazol-5-yl]-2-trifluoromethoxy-benzenesulfonamide;
1-[2-(4-Amino-7-cyclopentyl-7H-pyrrolo[2,3-d]pyrimidin-5-yl)-benzothiazol-6-yl]-3-(2-fluoro-5-methyl-phenyl)-urea;
1-[2-(4-Amino-7-cyclopentyl-7H-pyrrolo[2,3-d]pyrimidin-5-yl)-benzooxazol-6-yl]-3-(2-fluoro-5-methyl-phenyl)-urea;
1-[2-(4-Amino-7-cyclopentyl-7H-pyrrolo[2,3-d]pyrimidin-5-yl)-benzooxazol-6-yl]-3-(2-methoxy-5-methyl-phenyl)-urea;
1-[2-(4-Amino-7-cyclopentyl-7H-pyrrolo[2,3-d]pyrimidin-5-yl)-benzothiazol-6-yl]-3-(2-methoxy-5-methyl-phenyl)-urea;
1-[2-(4-Amino-7-cyclopentyl-7H-pyrrolo[2,3-d]pyrimidin-5-yl)-benzooxazol-6-yl]-3-(2,6-difluoro-phenyl)-urea;
1-[2-(4-Amino-7-cyclopentyl-7H-pyrrolo[2,3-d]pyrimidin-5-yl)-benzothiazol-6-yl]-3-(2,6-difluoro-phenyl)-urea;
1-[2-(4-Amino-7-cyclopentyl-7H-pyrrolo[2,3-d]pyrimidin-5-yl)-benzooxazol-6-yl]-3-m-tolyl-urea;
1-[2-(4-Amino-7-cyclopentyl-7H-pyrrolo[2,3-d]pyrimidin-5-yl)-benzothiazol-6-yl]-3-m-tolyl-urea;
1-[2-(4-Amino-7-cyclopentyl-7H-pyrrolo[2,3-d]pyrimidin-5-yl)-benzooxazol-6-yl]-3-(3-ethyl-phenyl)-urea; and
1-[2-(4-Amino-7-cyclopentyl-7H-pyrrolo[2,3-d]pyrimidin-5-yl)-benzothiazol-6-yl]-3-(3-ethyl-phenyl)-urea;
or
a pharmaceutically acceptable salt thereof.

23. A compound according to claim 1, wherein said compound is selected from the group consisting of:
N-[2-(4-Amino-7-cyclopentyl-7H-pyrrolo[2,3-d]pyrimidin-5-yl)-1H-benzoimidazol-5-yl]-2,6-difluoro-benzenesulfonamide;

N-[2-(4-Amino-7-cyclopentyl-7H-pyrrolo[2,3-d]pyrimidin-5-yl)-3H-benzoimidazol-5-yl]-2,4-difluoro-benzenesulfonamide;

1-[2-(4-Amino-7-cyclopentyl-7H-pyrrolo[2,3-d]pyrimidin-5-yl)-3H-benzoimidazol-5-yl]-3-p-tolyl-urea;

1-[2-(4-Amino-7-cyclopentyl-7H-pyrrolo[2,3-d]pyrimidin-5-yl)-3H-benzoimidazol-5-yl]-3-m-tolyl-urea;

1-[2-(4-Amino-7-cyclopentyl-7H-pyrrolo[2,3-d]pyrimidin-5-yl)-3H-benzoimidazol-5-yl]-3-(2-fluoro-phenyl)-urea;

1-[2-(4-Amino-7-cyclopentyl-7H-pyrrolo[2,3-d]pyrimidin-5-yl)-3H-benzoimidazol-5-yl]-3-(3ethyl-phenyl)-urea;

1-[2-(4-Amino-7-cyclopentyl-7H-pyrrolo[2,3-d]pyrimidin-5-yl)-3H-benzoimidazol-5-yl]-3-(2-methoxy-phenyl)-urea;

1-[2-(4-Amino-7-cyclopentyl-7H-pyrrolo[2,3-d]pyrimidin-5-yl)-3H-benzoimidazol-5-yl]-3-(3-methoxy-phenyl)-urea;

1-[2-(4-Amino-7-cyclopentyl-7H-pyrrolo[2,3-d]pyrimidin-5-yl)-3H-benzoimidazol-5-yl]-3-(4-methoxy-phenyl)-urea;

1-[2-(4-Amino-7-cyclopentyl-7H-pyrrolo[2,3-d]pyrimidin-5-yl)-3H-benzoimidazol-5-yl]-3-(2-fluoro-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-chloro-phenyl)-urea;

1-[2-(4-Amino-7-cyclopentyl-7H-pyrrolo[2,3-d]pyrimidin-5-yl)-3H-benzoimidazol-5-yl]-3-(4-chloro-phenyl)-urea;

1-[2-(4-Amino-7-cyclopentyl-7H-pyrrolo[2,3-d]pyrimidin-5-yl)-3H-benzoimidazol-5-yl]-3-(3,5-difluoro-phenyl)-urea;

1-[2-(4-Amino-7-cyclopentyl-7H-pyrrolo[2,3-d]pyrimidin-5-yl)-3H-benzoimidazol-5-yl]-3-(3,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2,5-difluoro-phenyl)-urea;

1-[2-(4-Amino-7-cyclopentyl-7H-pyrrolo[2,3-d]pyrimidin-5-yl)-3H-benzoimidazol-5-yl]-3-(2,6-difluoro-phenyl)-urea;

1-[2-(4-Amino-7-cyclopentyl-7H-pyrrolo[2,3-d]pyrimidin-5-yl)-3H-benzoimidazol-5-yl]-3-(2,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2-methoxy-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-ethoxy-phenyl)-urea;

N-[2-(4-Amino-7-cyclopentyl-7H-pyrrolo[2,3-d]pyrimidin-5-yl)-3H-benzoimidazol-5-yl]-2-chloro-benzenesulfonamide;

N-[2-(4-Amino-7-cyclopentyl-7H-pyrrolo[2,3-d]pyrimidin-5-yl)-3H-benzoimidazol-5-yl]-2,5-difluoro-benzenesulfonamide;

1-[2-(4-Amino-7-cyclopentyl-7H-pyrrolo[2,3-d]pyrimidin-5-yl)-benzothiazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-methoxy-5-methyl-phenyl)-urea;

1-[2-(4-Amino-7-cyclopentyl-7H-pyrrolo[2,3-d]pyrimidin-5-yl)-benzothiazol-6-yl]-3-(2-methoxy-5-methyl-phenyl)-urea;

1-[2-(4-Amino-7-cyclopentyl-7H-pyrrolo[2,3-d]pyrimidin-5-yl)-benzooxazol-6-yl]-3-(2,6-difluoro-phenyl)-urea;

1-[2-(4-Amino-7-cyclopentyl-7H-pyrrolo[2,3-d]pyrimidin-5-yl)-benzothiazol-6-yl]-3-(2,6-difluoro-phenyl)-urea;

1-[2-(4-Amino-7-cyclopentyl-7H-pyrrolo[2,3-d]pyrimidin-5-yl)-benzooxazol-6-yl]-3-m-tolyl-urea;

1-[2-(4-Amino-7-cyclopentyl-7H-pyrrolo[2,3-d]pyrimidin-5-yl)-benzothiazol-6-yl]-3-m-tolyl-urea;

1-[2-(4-Amino-7-cyclopentyl-7H-pyrrolo[2,3-d]pyrimidin-5-yl)-benzooxazol-6-yl]-3-(3-ethyl-phenyl)-urea; and 1-[2-(4-Amino-7-cyclopentyl-7H-pyrrolo[2,3-d]pyrimidin-5-yl)-benzothiazol-6-yl]-3-(3-ethyl-phenyl)-urea; or a pharmaceutically acceptable salt thereof.

24. A compound according to claim 1 selected from group consisting of:

N-[2-(4-Amino-7-cyclopentyl-7H-pyrrolo[2,3-d]pyrimidin-5-yl)-1H-benzoimidazol-5-yl]-2,6-difluoro-benzenesulfonamide;

N-[2-(4-Amino-7-cyclopentyl-7H-pyrrolo[2,3-d]pyrimidin-5-yl)-3H-benzoimidazol-5-yl]-2,4-difluoro-benzenesulfonamide;

1-[2-(4-Amino-7-cyclopentyl-7H-pyrrolo[2,3-d]pyrimidin-5-yl)-3H-benzoimidazol-5-yl]-3-m-tolyl-urea;

1-[2-(4-Amino-7-cyclopentyl-7H-pyrrolo[2,3-d]pyrimidin-5-yl)-3H-benzoimidazol-5-yl]-3-(2-fluoro-phenyl)-urea;

1-[2-(4-Amino-7-cyclopentyl-7H-pyrrolo[2,3-d]pyrimidin-5-yl)-3H-benzoimidazol-5-yl]-3-(3-ethyl-phenyl)-urea;

1-[2-(4-Amino-7-cyclopentyl-7H-pyrrolo[2,3-d]pyrimidin-5-yl)-3H-benzoimidazol-5-yl]-3-(3-methoxy-phenyl)-urea;

1-[2-(4-Amino-7-cyclopentyl-7H-pyrrolo[2,3-d]pyrimidin-5-yl)-3H-benzoimidazol-5-yl]-3-(4-methoxy-phenyl)-urea;

1-[2-(4-Amino-7-cyclopentyl-7H-pyrrolo[2,3-d]pyrimidin-5-yl)-3H-benzoimidazol-5-yl]-3-(2-fluoro-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-chloro-phenyl)-urea;

1-[2-(4-Amino-7-cyclopentyl-7H-pyrrolo[2,3-d]pyrimidin-5-yl)-3H-benzoimidazol-5-yl]-3-(2,6-difluoro-phenyl)-urea;

1-[2-(4-Amino-7-cyclopentyl-7H-pyrrolo[2,3-d]pyrimidin-5-yl)-3H-benzoimidazol-5-yl]-3-(2,4-difluoro-phenyl)-urea;

1-[2-(4-Amino-7-cyclopentyl-7H-pyrrolo[2,3-d]pyrimidin-5-yl)-3H-benzoimidazol-5-yl]-3-(2-methoxy-5-methyl-phenyl)-urea;

1-[2-(4-Amino-7-cyclopentyl-7H-pyrrolo[2,3-d]pyrimidin-5-yl)-3H-benzoimidazol-5-yl]-3-(2-ethoxy-phenyl)-urea;

1-[2-(4-Amino-7-cyclopentyl-7H-pyrrolo[2,3-d]pyrimidin-5-yl)-benzothiazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-fluoro-5-methyl-phenyl)-urea;

1-[2-(4-Amino-7-cyclopentyl-7H-pyrrolo[2,3-d]pyrimidin-5-yl)-benzooxazol-6-yl]-3-(2-methoxy-5-methyl-phenyl)-urea;

1-[2-(4-Amino-7-cyclopentyl-7H-pyrrolo[2,3-d]pyrimidin-5-yl)-benzothiazol-6-yl]-3-(2-methoxy-5-methyl-phenyl)-urea;

1-[2-(4-Amino-7-cyclopentyl-7H-pyrrolo[2,3-d]pyrimidin-5-yl)-benzooxazol-6-yl]-3-(2,6-difluoro-phenyl)-urea;

1-[2-(4-Amino-7-cyclopentyl-7H-pyrrolo[2,3-d]pyrimidin-5-yl)-benzothiazol-6-yl]-3-(2,6-difluoro-phenyl)-urea;

1-[2-(4-Amino-7-cyclopentyl-7H-pyrrolo[2,3-d]pyrimidin-5-yl)-benzooxazol-6-yl]-3-m-tolyl-urea;

1-[2-(4-Amino-7-cyclopentyl-7H-pyrrolo[2,3-d]pyrimidin-5-yl)-benzothiazol-6-yl]-3-m-tolyl-urea;

1-[2-(4-Amino-7-cyclopentyl-7H-pyrrolo[2,3-d]pyrimidin-5-yl)-benzooxazol-6-yl]-3-(3-ethyl-phenyl)-urea; and 1-[2-(4-Amino-7-cyclopentyl-7H-pyrrolo[2,3-d]pyrimidin-5-yl)-benzothiazol-6-yl]-3-(3-ethyl-phenyl)-urea;

or a pharmaceutically acceptable salt thereof.

25. A pharmaceutical composition, comprising an amount of a compound of claim 1, or a pharmaceutically acceptable salt thereof, and a pharmaceutically acceptable carrier.

26. A process for preparing a compound of the formula 1

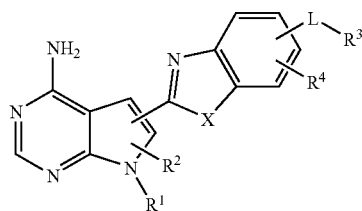

or a pharmaceutically acceptable salt thereof, wherein:

X is HN, $(C_1-C_6)$alkyl-N, $(C_3-C_8)$cycloalkyl-N, O or S;

L is —$(CH_2)_p$—, wherein p is an integer from 0 to 5; —O—; —S—; —S(O)—; —S(O)$_2$; —N(R)—; —N(C(O)OR)—; —N(C(O)R)—; —N(S(O)$_2$R)—; —CH$_2$O—; —CH$_2$S—; —CH$_2$N(R)—; —C(=NR)—; —CH$_2$N(C(O)R)—; —CH$_2$N(C(O)OR)—; —CH$_2$N(S(O)$_2$R)—; —CH(NHR)—; —CH(NHC(O)R)—; —CH(NHS(O)$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; —OC(O)N(R)—; —N(R)C(O)N(R)—; —N(R)C(O)O—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —S(O)N(C(O)R)—; —S(O)$_2$N(C(O)R)—; —C(O)O—; —N(R)P(OR$^5$)O—; —N(R)P(OR$^5$)—; —N(R)P(O)(OR$^5$)O—; —N(R)P(O)(OR$^5$)—; —N(C(O)R)P(OR$^5$)O—; —N(C(O)R)P(OR$^5$)—; —N(C(O)R)P(O)(OR$^5$)O—; —CH(R)S(O)—; —CH(R)S(O)$_2$—; —CH(R)N(C(O)R)—; —CH(R)O—; —CH(R)S—; —CH(R)N(R)—; —CH(R)N(C(O)R)—; —CH(R)N(C(O)OR)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; —CH(R)N(R)S(O)$_2$—; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; —CH(R)N(R)S(O)O—; —CH(R)N(R)S(O)$_2$O—; —CH(R)N(R)S(O)C(O)—; —CH(R)N(R)S(O)$_2$C(O)—; —CH(R)S(O)N(C(O)R)—; —CH(R)S(O)$_2$N(C(O)R)—; —CH(R)N(R)S(O)N(R)—; —CH(R)N(R)S(O)$_2$N(R)—; —CH(R)C(O)O—; —CH(R)N(R)P(OR$^5$)O—; —CH(R)N(R)P(OR$^5$)—; —CH(R)N(R)P(O)(OR$^5$)O—; —CH(R)N(R)P(O)(OR$^5$)—; —CH(R)N(C(O)R)P(OR$^5$)O—; —CH(R)N(C(O)R)P(OR$^5$)—; —CH(R)N(C(O)R)P(O)(OR$^5$)O— or —CH(R)N(C(O)R)P(OR$^5$)—; wherein each R is independently selected from the group consisting of H, $(C_1-C_6)$alkylcarbonyl, $(C_1-C_6)$alkyl, $(C_6-C_{10})$aryl and $(C_1-C_{10})$heteroaryl; wherein each of the aforesaid $(C_1-C_6)$alkylcarbonyl, $(C_1-C_6)$alkyl, $(C_6-C_{10})$aryl, and $(C_1-C_{10})$heteroaryl groups is independently optionally substituted with 1-3 substituents independently selected from halogen, $(C_1-C_6)$alkyl and $(C_1-C_6)$alkoxy;

$R^1$ is H, $(C_1-C_6)$alkyl, $(C_3-C_8)$cycloalkyl, $(C_6-C_{10})$aryl, $(C_1-C_{10})$heteroaryl, or $(C_3-C_8)$heterocycloalkyl, wherein each of the aforesaid $(C_1-C_6)$alkyl, $(C_3-C_8)$cycloalkyl, $(C_6-C_{10})$aryl, $(C_1-C_{10})$heteroaryl, and $(C_3-C_8)$heterocycloalkyl groups is optionally independently substituted with 1 to 5 $(C_1-C_6)$alkyl groups;

$R^2$ is H, halo, $(C_1-C_6)$alkyl, $(C_3-C_8)$cycloalkyl, $(C_6-C_{10})$aryl, $(C_1-C_{10})$heteroaryl, $(C_3-C_8)$heterocycloalkyl, —$(CR^{10}R^{11})_n NR^6R^7$ or —$(CR^{10}R^{11})_n C(O)NR^6R^7$; wherein n is an integer from 0-3; and each of the aforesaid $(C_1-C_6)$alkyl, $(C_3-C_8)$cycloalkyl, $(C_6-C_{10})$aryl, $(C_1-C_{10})$heteroaryl, and $(C_3-C_8)$heterocycloalkyl groups is optionally independently substituted with 1 to 5 $R^8$ substituents;

$R^3$ is H, $(C_1-C_6)$alkyl, $(C_3-C_8)$cycloalkyl, —$(CR^{10}R^{11})_t (C_6-C_{10})$aryl, —$(CR^{10}R^{11})_t (C_1-C_{10})$heteroaryl, or $(C_3-C_8)$heterocycloalkyl; and each of the aforesaid $(C_1-C_6)$alkyl, $(C_3-C_8)$cycloalkyl, —$(CR^{10}R^{11})_t (C_6-C_{10})$aryl, —$(CR^{10}R^{11})_t (C_1-C_{10})$heteroaryl, and $(C_3-C_8)$heterocycloalkyl groups is optionally independently substituted with 1 to 5 $R^{12}$ groups;

$R^4$ is H, halo, $(C_1-C_6)$alkyl, $(C_3-C_6)$cycloalkyl, $(C_1-C_6)$alkoxy, or $(C_3-C_6)$cycloalkoxy;

each $R^5$ is independently H, $(C_1-C_6)$alkylcarbonyl, $(C_1-C_6)$alkyl, $(C_6-C_{10})$aryl or $(C_1-C_{10})$heteroaryl; wherein each of the aforesaid $(C_1-C_6)$alkylcarbonyl, $(C_1-C_6)$alkyl, $(C_6-C_{10})$aryl, and $(C_1-C_{10})$heteroaryl groups is independently optionally substituted with 1-3 substituents independently selected from halogen, $(C_1-C_6)$alkyl and $(C_1-C_6)$alkoxy;

each $R^6$ and $R^7$ is independently H, $(C_1-C_6)$alkyl, —$(CR^{10}R^{11})_t (C_6-C_{10})$aryl, —$(CR^{10}R^{11})_t (C_1-C_{10})$heterocyclic, —$(CR^{10}R^{11})_t O(CR^{10}R^{11})_q OR^{10}$, or —$(CR^{10}R^{11})_t OR^{10}$, or $R^6$ and $R^7$ taken together on the same $R^5$ or on the same $R^{12}$ can form a heteroaryl or a heterocycloalkyl group; and the $(C_1-C_6)$alkyl, $(C_6-C_{10})$aryl and $(C_1-C_{10})$heterocyclic moieties of the foregoing $R^6$ and $R^7$ groups are optionally substituted by 1 to 3 substituents independently selected from halo, cyano, trifluoromethyl, —$C(O)R^9$, —$NR^{10}C(O)R^{11}$, —$C(O)$ $NR^{10}R^{11}$, —$NR^{10}R^{11}(C_1$-$C_6)$alkyl, —$(CR^{10}R^{11})_t(C_6$-$C_{10})$aryl, —$(CR^{10}R^{11})_t(C_1$-$C_{10})$heterocyclic, —$(CR^{10}R^{11})_tO(CR^{10}R^{11})_qOR^{10}$, and —$(CR^{10}R^{11})_tOR^{10}$; and further that where $R^6$ and $R^7$ are both attached to the same nitrogen, then $R^6$ and $R^7$ are not both bonded to the nitrogen directly through an oxygen;

each $R^8$ and $R^{12}$ is independently halo, cyano, trifluoromethoxy, trifluoromethyl, —$C(O)R^9$, —$NR^6C(O)R^7$, —$C(O)NR^6R^7$, —$NR^6R^7$, —$OR^{10}$, —$SO_2NR^6R^7$, —$SO_2R^6$, —$NR^6SO_2R^7$, $(C_1$-$C_6)$alkyl, $(C_2$-$C_6)$alkenyl, $(C_2$-$C_6)$alkynyl, —$(CR^{10}R^{11})_tO(CR^{10}R^{11})_qNR^6R^7$, —$(CR^{10}R^{11})_tO(CR^{10}R^{11})_qOR^{10}$, —$(CR^{10}R^{11})_tOR^{10}$, —$S(O)_j(C_1$-$C_6)$alkyl, —$(CR^{10}R^{11})_t(C_6$-$C_{10})$aryl, —$(CR^{10}R^{11})_t(C_1$-$C_{10})$heterocyclic, —$(CR^{10}R^{11})_tO(CH_2)_q(C_1$-$C_{10})$heterocyclic, —$C(O)(CR^{10}R^{11})_t(C_1$-$C_{10})$heterocyclic, —$(CR^{10}R^{11})_jNR^7(CR^{10}R^{11})_qNR^6R^7$, —$(CR^{10}R^{11})_jNR^7CR^{10}R^{11}C(O)NR^6R^7$, —$(CR^{10}R^{11})_jNR^7(CR^{10}R^{11})_qNR^{10}C(O)R^9$, —$(CR^{10}R^{11})_jNR^7(CR^{10}R^{11})_tO(CR^{10}R^{11})_qOR^{10}$, —$(CR^{10}R^{11})_jNR^7(CR^{10}R^{11})_qS(O)_j(C_1$-$C_6)$alkyl, —$(CR^{10}R^{11})_jNR^7(CR^{10}R^{11})_tR^6$, —$SO_2(CR^{10}R^{11})_t(C_6$-$C_{10})$aryl, or —$SO_2(CR^{10}R^{11})_t(C_1$-$C_{10})$heterocyclic; the —$(CR^{10}R^{11})_q$— and —$(CR^{10}R^{11})_t$— moieties of the foregoing $R^8$ and $R^{12}$ groups optionally include a carbon-carbon double or triple bond; and the $(C_1$-$C_6)$alkyl, $(C_6$-$C_{10})$aryl and $(C_1$-$C_{10})$heterocyclic moieties of the aforesaid $R^8$ and $R^{12}$ groups are optionally substituted on a carbon atom by 1 to 3 substituents independently selected from halo, cyano, trifluoromethyl, —$C(O)R^9$, —$NR^6C(O)R^7$, —$C(O)NR^6R^7$, —$(CR^{10}R^{11})_tNR^6R^7$, —$SO_2R^6$, —$SO_2NR^6R^7$, $(C_1$-$C_6)$alkyl, —$(CR^{10}R^{11})(C_1$-$C_{10})$heterocyclic, $(CR^{10}R^{11})_tO(CR^{10}R^{11})_qOR^{10}$, and —$(CR^{10}R^{11})_tOR^{10}$;

each $R^9$ is independently H, $(C_1$-$C_{10})$alkyl, —$(CR^{10}R^{11})_t(C_6$-$C_{10})$aryl, or —$(CR^{10}R^{11})_t(C_1$-$C_{10})$heterocyclic, each $R^{10}$ and $R^{11}$ is independently H or $(C_1$-$C_6)$alkyl;

each j is independently 0, 1 or 2;

each t is independently 0, 1 2, 3, 4, 5 or 6; and each q is independently 2, 3, 4, 5, or 6;

which comprises treating a compound of the formula 1A wherein Z is halo

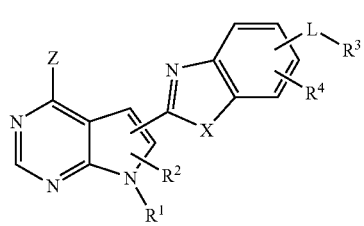

1A with ammonia or ammonium hydroxide.

27. The process of claim 26, wherein Z is Cl.

28. The process of claim 26, wherein formula 1 is represented by formula 2

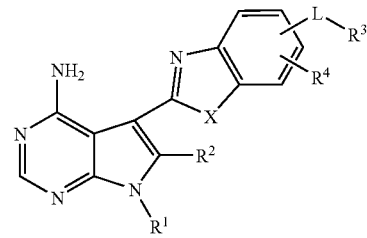

2 and formula 1A is represented by formula 1B

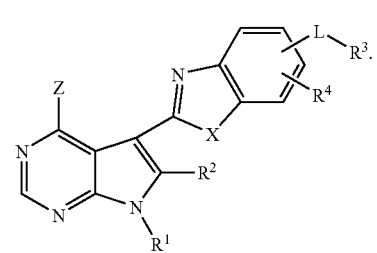

1B

29. The process of claim 26, wherein formula 1 is represented by formula 3

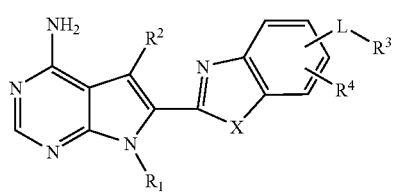

3 and formula 1A is represented by formula 1C

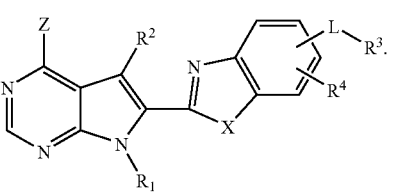

1C

30. A process for preparing a compound of the formula

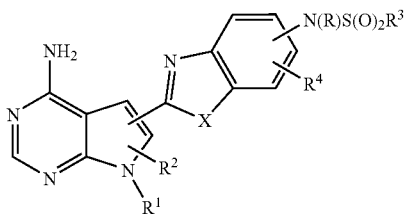

or a pharmaceutically acceptable salt thereof, wherein:

X is HN, $(C_1\text{-}C_6)$alkyl-N, $(C_3\text{-}C_8)$cycloalkyl-N, O or S;

$R^1$ is H, $(C_1\text{-}C_6)$alkyl, $(C_3\text{-}C_8)$cycloalkyl, $(C_6\text{-}C_{10})$aryl, $(C_1\text{-}C_{10})$heteroaryl, or $(C_3\text{-}C_8)$heterocycloalkyl, wherein each of the aforesaid $(C_1\text{-}C_6)$alkyl, $(C_3\text{-}C_8)$cycloalkyl, $(C_6\text{-}C_{10})$aryl, $(C_1\text{-}C_{10})$heteroaryl, and $(C_3\text{-}C_8)$ heterocycloalkyl groups is optionally independently substituted with 1 to 5 $(C_1\text{-}C_6)$alkyl groups;

$R^2$ is H, halo, $(C_1\text{-}C_6)$alkyl, $(C_3\text{-}C_8)$cycloalkyl, $(C_6\text{-}C_{10})$aryl, $(C_1\text{-}C_{10})$heteroaryl, $(C_3\text{-}C_8)$heterocycloalkyl, —$(CR^{10}R^{11})_n NR^6R^7$ or —$(CR^{10}R^{11})_n C(O)NR^6R^7$; wherein n is an integer from 0-3; and each of the aforesaid $(C_1\text{-}C_6)$alkyl, $(C_3\text{-}C_8)$cycloalkyl, $(C_6\text{-}C_{10})$aryl, $(C_1\text{-}C_{10})$heteroaryl, and $(C_3\text{-}C_8)$heterocycloalkyl groups is optionally independently substituted with 1 to 5 $R^8$ substituents;

$R^3$ is H, $(C_1\text{-}C_6)$alkyl, $(C_3\text{-}C_8)$cycloalkyl, —$(CR^{10}R^{11})_t (C_6\text{-}C_{10})$aryl, —$(CR^{10}R^{11})_t(C_1\text{-}C_{10})$heteroaryl, or $(C_3\text{-}C_8)$heterocycloalkyl; and each of the aforesaid $(C_1\text{-}C_6)$alkyl, $(C_3\text{-}C_8)$cycloalkyl, —$(CR^{10}R^{11})_t(C_6\text{-}C_{10})$aryl, —$(CR^{10}R^{11})_t(C_1\text{-}C_{10})$heteroaryl, and $(C_3\text{-}C_8)$heterocycloalkyl groups is optionally independently substituted with 1 to 5 $R^{12}$ groups;

$R^4$ is H, halo, $(C_1\text{-}C_6)$alkyl, $(C_3\text{-}C_6)$cycloalkyl, $(C_1\text{-}C_6)$alkoxy, or $(C_3\text{-}C_6)$cycloalkoxy;

each $R^6$ and $R^7$ is independently H, $(C_1\text{-}C_6)$alkyl, —$(CR^{10}R^{11})_t(C_6\text{-}C_{10})$aryl, —$(CR^{10}R^{11})_t(C_1\text{-}C_{10})$heterocyclic, —$(CR^{10}R^{11})_tO(CR^{10}R^{11})_qOR^{10}$, or —$(CR^{10}R^{11})_tOR^{10}$, or $R^6$ and $R^7$ taken together on the same $R^8$ or on the same $R^{12}$ can form a heteroaryl or a heterocycloalkyl group; and the $(C_1\text{-}C_6)$alkyl, $(C_6\text{-}C_{10})$aryl and $(C_1\text{-}C_{10})$heterocyclic moieties of the foregoing $R^6$ and $R^7$ groups are optionally substituted by 1 to 3 substituents independently selected from halo, cyano, trifluoromethyl, —$C(O)R^9$, —$NR^{10}C(O)R^{11}$, —$C(O)NR^{10}R^{11}$, —$NR^{10}R^{11}$, $(C_1\text{-}C_6)$alkyl, —$(CR^{10}R^{11})_t(C_6\text{-}C_{10})$aryl, —$(CR^{10}R^{11})_t(C_1\text{-}C_{10})$heterocyclic, —$(CR^{10}R^{11})_tO(CR^{10}R^{11})_qOR^{10}$, and —$(CR^{10}R^{11})_tOR^{10}$; and further that where $R^6$ and $R^7$ are both attached to the same nitrogen, then $R^6$ and $R^7$ are not both bonded to the nitrogen directly through an oxygen;

each $R^8$ and $R^{12}$ is independently halo, cyano, trifluoromethoxy, trifluoromethyl, —$C(O)R^9$, —$NR^6C(O)R^7$, —$C(O)NR^6R^7$, —$NR^6R^7$, —$OR^{10}$, —$SO_2NR^6R^7$, —$SO_2R^6$, —$NR^6SO_2R^7$, $(C_1\text{-}C_6)$alkyl, $(C_2\text{-}C_6)$alkenyl, $(C_2\text{-}C_8)$alkynyl, —$(CR^{10}R^{11})_jO(CR^{10}R^{11})_q NR^6R^7$, —$(CR^{10}R^{11})_tO(CR^{10}R^{11})_qOR^{10}$, —$(CR^{10}R^{11})_tOR^{10}$, —$S(O)_j(C_1\text{-}C_8)$alkyl, —$(CR^{10}R^{11})_t(C_6\text{-}C_{10})$aryl, —$(CR^{10}R^{11})_t(C_1\text{-}C_{10})$heterocyclic, —$(CR^{10}R^{11})_tO(CH_2)_q(C_1\text{-}C_{10})$heterocyclic, —$C(O)(CR^{10}R^{11})_t(C_1\text{-}C_{10})$heterocyclic, —$(CR^{10}R^{11})_jNR^7(CR^{10}R^{11})_qNR^6R^7$, —$(CR^{10}R^{11})_jNR^7CR^{10}R^{11}C(O)NR^6R^7$, —$(CR^{10}R^{11})_jNR^7(CR^{10}R^{11})_qNR^{10}C(O)R^9$, —$(CR^{10}R^{11})_jNR^7(CR^{10}R^{11})_tO(CR^{10}R^{11})_qOR^{10}$, —$(CR^{10}R^{11})_jNR^7(CR^{10}R^{11})_qS(O)_j(C_1\text{-}C_6)$alkyl, —$(CR^{10}R^{11})_jNR^7(CR^{10}R^{11})_tR^6$, —$SO_2(CR^{10}R^{11})_t(C_6\text{-}C_{10})$aryl, or —$SO_2(CR^{10}R^{11})_t(C_1\text{-}C_{10})$heterocyclic; the —$(CR^{10}R^{11})_q$— and —$(CR^{10}R^{11})_t$— moieties of the foregoing $R^8$ and $R^{12}$ groups optionally include a carbon-carbon double or triple bond; and the $(C_1\text{-}C_6)$alkyl, $(C_6\text{-}C_{10})$aryl and $(C_1\text{-}C_{10})$heterocyclic moieties of the aforesaid $R^8$ and $R^{12}$ groups are optionally substituted on a carbon atom by 1 to 3 substituents independently selected from halo, cyano, trifluoromethyl, —$C(O)R^9$, —$NR^6C(O)R^7$, —$C(O)NR^6R^7$, —$(CR^{10}R^{11})_tNR^6R^7$, —$SO_2R^6$, —$SO_2NR^6R^7$, $(C_1\text{-}C_6)$alkyl, —$(CR^{10}R^{11})_t(C_1\text{-}C_{10})$heterocyclic, —$(CR^{10}R^{11})_tO(CR^{10}R^{11})_qOR^{10}$, and —$(CR^{10}R^{11})_tOR^{10}$;

each $R^9$ is independently H, $(C_1\text{-}C_{10})$alkyl, —$(CR^{10}R^{11})_t(C_6\text{-}C_{10})$aryl, or —$(CR^{10}R^{11})_t(C_1\text{-}C_{10})$heterocyclic;

each $R^{10}$ and $R^{11}$ is independently H or $(C_1\text{-}C_6)$alkyl;

each j is independently 0, 1 or 2;

each t is independently 0, 1, 2, 3, 4, 5 or 6; and each q is independently 2, 3, 4, 5, or 6;

which comprises treating a compound of the formula 10A

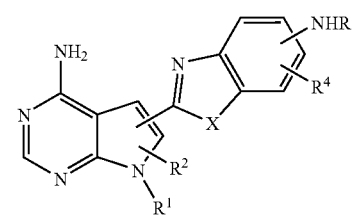

wherein X, R, $R^1$, $R^2$, $R^4$ have the same meaning as set forth above for formula 13; with a compound of formula $R^3$—$S(O)_2$—Cl, wherein $R^3$ has the same meaning as set forth above for formula 13.

31. A process for preparing a compound of the formula 14

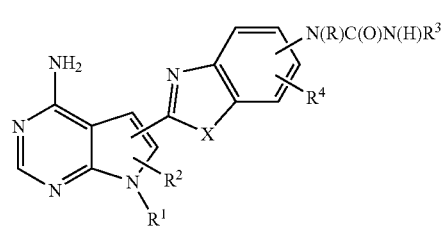

or a pharmaceutically acceptable salt, prodrug, solvate or hydrate thereof, wherein:

X is HN, $(C_1\text{-}C_6)$alkyl-N, $(C_3\text{-}C_8)$cycloalkyl-N, O or S;

$R^1$ is H, $(C_1\text{-}C_6)$alkyl, $(C_3\text{-}C_8)$cycloalkyl, $(C_6\text{-}C_{10})$aryl, $(C_1\text{-}C_{10})$heteroaryl, or $(C_3\text{-}C_8)$heterocycloalkyl, wherein each of the aforesaid $(C_1\text{-}C_6)$alkyl, $(C_3\text{-}C_8)$cycloalkyl, $(C_6\text{-}C_{10})$aryl, $(C_1\text{-}C_{10})$heteroaryl, and $(C_3\text{-}C_8)$ heterocycloalkyl groups is optionally independently substituted with 1 to 5 $(C_1\text{-}C_6)$alkyl groups;

53

R² is H, halo, $(C_1-C_6)$alkyl, $(C_3-C_8)$cycloalkyl, $(C_6-C_{10})$aryl, $(C_1-C_{10})$heteroaryl, $(C_3-C_8)$heterocycloalkyl, $-(CR^{10}R^{11})_nNR^6R^7$ or $-(CR^{10}R^{11})_nC(O)NR^6R^7$; wherein n is an integer from 0-3; and each of the aforesaid $(C_1-C_6)$alkyl, $(C_3-C_8)$cycloalkyl, $(C_6-C_{10})$aryl, $(C_1-C_{10})$heteroaryl, and $(C_3-C_8)$heterocycloalkyl groups is optionally independently substituted with 1 to 5 $R^8$ substituents;

R³ is H, $(C_1-C_6)$alkyl, $(C_3-C_8)$cycloalkyl, $-(CR^{10}R^{11})_t(C_6-C_{10})$aryl, $-(CR^{10}R^{11})_t(C_1-C_{10})$heteroaryl, or $(C_3-C_8)$heterocycloalkyl; and each of the aforesaid $(C_1-C_6)$alkyl, $(C_3-C_8)$cycloalkyl, $-(CR^{10}R^1)_t(C_6-C_{10})$aryl, $-(CR^{10}R^{11})_t(C_1-C_{10})$heteroaryl, and $(C_3-C_8)$heterocycloalkyl groups is optionally independently substituted with 1 to 5 $R^{12}$ groups;

R⁴ is H, halo, $(C_1-C_6)$alkyl, $(C_3-C_6)$cycloalkyl, $(C_1-C_6)$alkoxy, or $(C_3-C_6)$cycloalkoxy;

each $R^6$ and $R^7$ is independently H, $(C_1-C_6)$alkyl, $-(CR^{10}R^{11})_t(C_6-C_{10})$aryl, $-(CR^{10}R^{11})_t(C_1-C_{10})$heterocyclic, $-(CR^{10}R^{11})_tO(CR^{10}R^{11})_qOR^{10}$, or $-(CR^{10}R^{11})_tOR^{10}$ or $R^6$ and $R^7$ taken together on the same $R^8$ or on the same $R^{12}$ can form a heteroaryl or a heterocycloalkyl group; and the $(C_1-C_6)$alkyl, $(C_6-C_{10})$aryl and $(C_1-C_{10})$heterocyclic moieties of the foregoing $R^6$ and $R^7$ groups are optionally substituted by 1 to 3 substituents independently selected from halo, cyano, trifluoromethyl, $-C(O)R^9$, $-NR^{10}C(O)R^{11}$, $-C(O)NR^{10}R^{11}$, $-NR^{10}R^{11}$, $(C_1-C_6)$alkyl, $-(CR^{10}R^{11})_t(C_6-C_{10})$aryl, $-(CR^{10}R^{11})_t(C_1-C_{10})$heterocyclic, $-(CR^{10}R^{11})_tO(CR^{10}R^{11})_qOR^{10}$, and $-(CR^{10}R^{11})_tOR^{10}$; and further that where $R^6$ and $R^7$ are both attached to the same nitrogen, then $R^6$ and $R^7$ are not both bonded to the nitrogen directly through an oxygen;

each $R^8$ and $R^{12}$ is independently halo, cyano, trifluoromethoxy, trifluoromethyl, $-C(O)R^9$, $-NR^6C(O)R^7$, $-C(O)NR^6R^7$, $-NR^6R^7$, $-OR^{10}$, $-SO_2NR^6R^7$, $-SO_2R^6$, $-NR^6SO_2R^7$, $(C_1-C_6)$alkyl, $(C_2-C_6)$alkenyl, $(C_2-C_6)$alkynyl, $-(CR^{10}R^{11})_tO(CR^{10}R^{11})_qNR^6R^7$, $-(CR^{10}R^{11})_tO(CR^{10}R^{11})_qOR^{10}$, $-(CR^{10}R^{11})_tOR^{10}$, $-S(O)_j(C_1-C_6)$alkyl, $-(CR^{10}R^{11})_t(C_6-C_{10})$aryl, $-(CR^{10}R^{11})_t(C_1-C_{10})$heterocyclic, $-(CR^{10}R^{11})_tO(CH_2)_q(C_1-C_{10})$heterocyclic, $-C(O)(CR^{10}R^{11})_t(C_1-C_{10})$heterocyclic, $-(CR^{10}R^{11})_tNR^7CR^{10}R^{11}C(O)NR^6R^7$, $-(CR^{10}R^{11})_jNR^7$ $CR^{10}R^{11}C(O)NR^6R^7$, $-(CR^{10}R^{11})_jNR^7(CR^{10}R^{11})_tNR^{10}C(O)R^9$, $-(CR^{10}R^{11})_jNR^7(CR^{10}R^{11})_tO(CR^{10}R^{11})_qOR^{10}$, $-(CR^{10}R^{11})_jNR^7(CR^{10}R^{11})_qS(O)_j(C_1-C_6)$alkyl, $-(CR^{10}R^{11})_jNR^7(CR^{10}R^{11})_tR^6$, $-SO_2(CR^{10}R^{11})_t(C_6-C_{10})$aryl, or $-SO_2(CR^{10}R^{11})_t(C_1-C_{10})$heterocyclic; the $-(CR^{10}R^{11})_q-$ and $-(CR^{10}R^{11})_t-$ moieties of the foregoing $R^8$ and $R^{12}$ groups optionally include a carbon-carbon double or triple bond; and the $(C_1-C_6)$alkyl, $(C_6-C_{10})$aryl and $(C_1-C_{10})$heterocyclic moieties of the aforesaid $R^8$ and $R^{12}$ groups are optionally substituted on a carbon atom by 1 to 3 substituents independently selected from halo, cyano, trifluoromethyl, $-C(O)R^9$, $-NR^6C(O)R^7$, $-C(O)NR^6R^7$, $-(CR^{10}R^{11})_tNR^6R^7$, $-SO_2R^6$, $-SO_2NR^6R^7$, $(C_1-C_6)$alkyl, $-(CR^{10}R^{11})_t(C_1-C_{10})$heterocyclic, $-(CR^{10}R^{11})_tO(CR^{10}R^{11})_qOR^{10}$, and $-(CR^{10}R^{11})_tOR^{10}$;

each $R^9$ is independently H, $(C_1-C_{10})$alkyl, $-(CR^{10}R^{11})_t(C_6-C_{10})$aryl, or $-(CR^{10}R^{11})_t(C_1-C_{10})$heterocyclic;

each $R^{10}$ and $R^{11}$ is independently H or $(C_1-C_6)$alkyl;

each j is independently 0, 1 or 2;

each t is independently 0, 1, 2, 3, 4, 5 or 6; and each q is independently 2, 3, 4, 5, or 6;

54 which comprises reacting a compound of the formula 10A

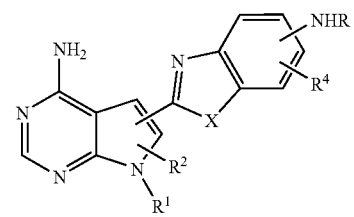

wherein X, R, $R^1$, $R^2$, $R^4$ have the same meaning as set forth above for formula 14; with a compound of formula $R^3$—NCO, wherein $R^3$ has the same meaning as set forth above for formula 14.

32. A process for preparing a compound of the formula 1D

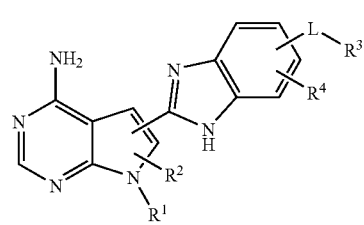

or a pharmaceutically acceptable salt thereof, wherein:

L is $-(CH_2)_p-$, wherein p is an integer from 0 to 5; $-O-$; $-S-$; $-S(O)-$; $-S(O)_2-$; $-N(R)-$; $-N(C(O)OR)-$; $-N(C(O)R)-$; $-N(S(O)_2R)-$; $-CH_2O-$; $-CH_2S-$; $-CH_2N(R)-$; $-C(=NR)-$; $-CH_2N(C(O)R)-$; $-CH_2N(C(O)OR)-$; $-CH_2N(S(O)_2R)-$; $-CH(NHR)-$; $-CH(NHC(O)R)-$; $-CH(NHS(O)_2R)-$; $-CH(NHC(O)OR)-$; $-CH(OC(O)R)-$; $-CH(OC(O)NHR)-$; $-CH=CH-$; $-C(=NOR)-$; $-C(O)-$; $-CH(OR)-$; $-C(O)N(R)-$; $-N(R)C(O)-$; $-N(R)S(O)-$; $-N(R)S(O)_2-$; $-OC(O)N(R)-$; $-N(R)C(O)N(R)-$; $-N(R)C(O)O-$; $-S(O)N(R)-$; $-S(O)_2N(R)-$; $-N(C(O)R)S(O)-$; $-N(C(O)R)S(O)_2-$; $-N(R)S(O)N(R)-$; $-N(R)S(O)_2N(R)-$; $-C(O)N(R)C(O)-$; $-S(O)N(R)C(O)-$; $-S(O)_2N(R)C(O)-$; $-OS(O)N(R)-$; $-OS(O)_2N(R)-$; $-N(R)S(O)O-$; $-N(R)S(O)_2O-$; $-N(R)S(O)C(O)-$; $-N(R)S(O)_2C(O)-$; $-S(O)N(C(O)R)-$; $-S(O)_2N(C(O)R)-$; $-C(O)O-$; $-N(R)P(OR^5)O-$; $-N(R)P(OR^5)-$; $-N(R)P(O)(OR^5)O-$; $-N(R)P(O)(OR^5)-$; $-N(C(O)R)P(OR^5)O-$; $-N(C(O)R)P(OR^5)-$; $-N(C(O)R)P(O)(OR^5)O-$; $-CH(R)S(O)-$; $-CH(R)S(O)_2-$; $-CH(R)N(C(O)OR^5)-$; $-CH(R)N(C(O)R)-$; $-CH(R)N(SO_2R)-$; $-CH(R)O-$; $-CH(R)S-$; $-CH(R)N(R)-$; $-CH(R)N(C(O)R)-$; $-CH(R)N(C(O)OR)-$; $-CH(R)C(=NOR)-$; $-CH(R)C(O)-$; $-CH(R)CH(OR)-$; $-CH(R)C(O)N(R)-$; $-CH(R)N(R)C(O)-$; $-CH(R)N(R)S(O)-$; $-CH(R)N(R)S(O)_2-$; $-CH(R)OC(O)N(R)-$; $-CH(R)N(R)C(O)N(R)-$; $-CH(R)N(R)C(O)O-$; $-CH(R)S(O)N(R)-$; $-CH(R)S(O)_2N(R)-$; $-CH(R)N(C(O)R)S(O)-$; $-CH(R)N(C(O)R)S(O)_2-$; $-CH(R)N(R)S(O)N(R)-$; $-CH(R)N(R)S(O)_2N(R)-$; $-CH (R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; —CH(R)N(R)S(O)O—; —CH(R)N(R)S(O)$_2$O—; —CH(R)N(R)S(O)C(O)—; —CH(R)N(R)S(O)$_2$C(O)—; —CH(R)S(O)N(C(O)R)—; —CH(R)S(O)$_2$N(C(O)R)—; —CH(R)N(R)S(O)N(R)—; —CH(R)N(R)S(O)$_2$N(R)—; —CH(R)C(O)O—; —CH(R)N(R)P(OR$^5$)O—; —CH(R)N(R)P(OR$^5$)—; —CH(R)N(R)P(O)(OR$^5$)O—; —CH(R)N(R)P(O)(OR$^5$)—; —CH(R)N(C(O)R)P(OR$^5$)O—; —CH(R)N(C(O)R)P(OR$^5$)—; —CH(R)N(C(O)R)P(O)(OR$^5$)O— or —CH(R)N(C(O)R)P(OR$^5$)—; wherein each R is independently selected from the group consisting of H, (C$_1$-C$_6$)alkylcarbonyl, (C$_1$-C$_6$)alkyl, (C$_6$-C$_{10}$)aryl and (C$_1$-C$_{10}$)heteroaryl; wherein each of the aforesaid (C$_1$-C$_6$)alkylcarbonyl, (C$_1$-C$_6$)alkyl, (C$_6$-C$_{10}$)aryl, and (C$_1$-C$_{10}$)heteroaryl groups is independently optionally substituted with 1-3 substituents independently selected from halogen, (C$_1$-C$_6$)alkyl and (C$_1$-C$_6$)alkoxy;

R$^1$ is H, (C$_1$-C$_6$)alkyl, (C$_3$-C$_8$)cycloalkyl, (C$_6$-C$_{10}$)aryl, (C$_1$-C$_{10}$)heteroaryl, or (C$_3$-C$_8$)heterocycloalkyl, wherein each of the aforesaid (C$_1$-C$_6$)alkyl, (C$_3$-C$_8$)cycloalkyl, (C$_6$-C$_{10}$)aryl, (C$_1$-C$_{10}$)heteroaryl, and (C$_3$-C$_8$)heterocycloalkyl groups is optionally independently substituted with 1 to 5 (C$_1$-C$_6$)alkyl groups;

R$^2$ is H, halo, (C$_1$-C$_6$)alkyl, (C$_3$-C$_8$)cycloalkyl, (C$_6$-C$_{10}$)aryl, (C$_1$-C$_{10}$)heteroaryl, (C$_3$-C$_8$)heterocycloalkyl, —(CR$^{10}$R$^{11}$)$_n$NR$^6$R$^7$ or —(CR$^{10}$R$^{11}$)$_n$C(O)NR$^6$R$^7$; wherein n is an integer from 0-3; and each of the aforesaid (C$_1$-C$_6$)alkyl, (C$_3$-C$_8$)cycloalkyl, (C$_6$-C$_{10}$)aryl, (C$_1$-C$_{10}$)heteroaryl, and (C$_3$-C$_8$)heterocycloalkyl groups is optionally independently substituted with 1 to 5 R$^8$ substituents;

R$^3$ is H, (C$_1$-C$_6$)alkyl, (C$_3$-C$_8$)cycloalkyl, —(CR$^{10}$R$^{11}$)$_t$(C$_6$-C$_{10}$)aryl, —(CR$^{10}$R$^{11}$)$_t$(C$_1$-C$_{10}$)heteroaryl, or (C$_3$-C$_8$)heterocycloalkyl; and each of the aforesaid (C$_1$-C$_6$)alkyl, (C$_3$-C$_8$)cycloalkyl, —(CR$^{10}$R$^{11}$)$_t$(C$_6$-C$_{10}$)aryl, —(CR$^{10}$R$^{11}$)$_t$(C$_1$-C$_{10}$)heteroaryl, and (C$_3$-C$_8$)heterocycloalkyl groups is optionally independently substituted with 1 to 5 R$^{12}$ groups;

R$^4$ is H, halo, (C$_1$-C$_6$)alkyl, (C$_3$-C$_6$)cycloalkyl, (C$_1$-C$_6$)alkoxy, or (C$_3$-C$_6$)cycloalkoxy;

each R$^5$ is independently H, (C$_1$-C$_6$)alkylcarbonyl, (C$_1$-C$_6$)alkyl, (C$_6$-C$_{10}$)aryl or (C$_1$-C$_{10}$)heteroaryl; wherein each of the aforesaid (C$_1$-C$_6$)alkylcarbonyl, (C$_1$-C$_6$)alkyl, (C$_6$-C$_{10}$)aryl, and (C$_1$-C$_{10}$)heteroaryl groups is independently optionally substituted with 1-3 substituents independently selected from halogen, (C$_1$-C$_6$)alkyl and (C$_1$-C$_6$)alkoxy;

each R$^6$ and R$^7$ is independently H, (C$_1$-C$_6$)alkyl, —(CR$^{10}$R$^{11}$)$_t$(C$_6$-C$_{10}$)aryl, —(CR$^{10}$R$^{11}$)$_t$(C$_1$-C$_{10}$)heterocyclic, —(CR$^{10}$R$^{11}$)$_t$O(CR$^{10}$R$^{11}$)$_q$OR$^{10}$, or —(CR$^{10}$R$^{11}$)$_t$OR$^{10}$, or R$^6$ and R$^7$ taken together on the same R$^8$ or on the same R$^{12}$ can form a heteroaryl or a heterocycloalkyl group; and the (C$_1$-C$_6$)alkyl, (C$_6$-C$_{10}$)aryl and (C$_1$-C$_{10}$)heterocyclic moieties of the foregoing R$^6$ and R$^7$ groups are optionally substituted by 1 to 3 substituents independently selected from halo, cyano, trifluoromethyl, —C(O)R$^9$, —NR$^{10}$C(O)R$^{11}$, —C(O)NR$^{10}$R$^{11}$, —NR$^{10}$R$^{11}$, (C$_1$-C$_6$)alkyl, —(CR$^{10}$R$^{11}$)$_t$(C$_6$-C$_{10}$)aryl, —(CR$^{10}$R$^{11}$)$_t$(C$_1$-C$_{10}$)heterocyclic, —(CR$^{10}$R$^{11}$)$_t$O(CR$^{10}$R$^{11}$)$_q$OR$^{10}$, and —(CR$^{10}$R$^{11}$)$_t$OR$^{10}$; and further that where R$^6$ and R$^7$ are both attached to the same nitrogen, then R$^6$ and R$^7$ are not both bonded to the nitrogen directly through an oxygen;

each R$^8$ and R$^{12}$ is independently halo, cyano, trifluoromethoxy, trifluoromethyl, —C(O)R$^9$, —NR$^6$C(O)R$^7$, —C(O)NR$^6$R$^7$, —NR$^6$R$^7$, —OR$^{10}$, —SO$_2$NR$^6$R$^7$, —SO$_2$R$^6$, —NR$^6$SO$_2$R$^7$, (C$_1$-C$_6$)alkyl, (C$_2$-C$_6$)alkenyl, (C$_2$-C$_6$)alkynyl, —(CR$^{10}$R$^{11}$)$_t$O(CR$^{10}$R$^{11}$)$_q$NR$^6$R$^7$, —(CR$^{10}$R$^{11}$)$_t$O(CR$^{10}$R$^{11}$)$_q$OR$^{10}$, —(CR$^{10}$R$^{11}$)$_t$OR$^{10}$, —S(O)$_j$(C$_1$-C$_6$)alkyl, —(CR$^{10}$R$^{11}$)$_t$(C$_6$-C$_{10}$)aryl, —(CR$^{10}$R$^{11}$)$_t$(C$_1$-C$_{10}$)heterocyclic, —(CR$^{10}$R$^{11}$)$_t$O(CH$_2$)$_q$(C$_1$-C$_{10}$)heterocyclic, —C(O)(CR$^{10}$R$^{11}$)$_t$(C$_1$-C$_{10}$)heterocyclic, —(CR$^{10}$R$^{11}$)$_t$NR$^7$(CR$^{10}$R$^{11}$)$_q$NR$^6$R$^7$, —(CR$^{10}$R$^{11}$)$_t$NR$^7$CR$^{10}$R$^{11}$C(O)NR$^6$R$^7$, —(CR$^{10}$R$^{11}$)$_t$NR$^7$(CR$^{10}$R$^{11}$)$_t$NR$^{10}$C(O)R$^9$, —(CR$^{10}$R$^{11}$)$_t$NR$^7$(CR$^{10}$R$^{11}$)$_t$O(CR$^{10}$R$^{11}$)$_q$OR$^{10}$, —(CR$^{10}$R$^{11}$)$_t$NR$^7$(CR$^{10}$R$^{11}$)$_q$S(O)$_j$(C$_1$-C$_6$)alkyl, —(CR$^{10}$R$^{11}$)$_t$NR$^7$(CR$^{10}$R$^{11}$)$_t$R$^6$, —SO$_2$(CR$^{10}$R$^{11}$)$_t$(C$_6$-C$_{10}$)aryl, or —SO$_2$(CR$^{10}$R$^{11}$)$_t$(C$_1$-C$_{10}$)heterocyclic; the —(CR$^{10}$R$^{11}$)$_q$— and —(CR$^{10}$R$^{11}$)$_t$— moieties of the foregoing R$^8$ and R$^{12}$ groups optionally include a carbon-carbon double or triple bond; and the (C$_1$-C$_6$)alkyl, (C$_6$-C$_{10}$)aryl and (C$_1$-C$_{10}$)heterocyclic moieties of the aforesaid R$^8$ and R$^{12}$ groups are optionally substituted on a carbon atom by 1 to 3 substituents independently selected from halo, cyano, trifluoromethyl, —C(O)R$^9$, —NR$^6$C(O)R$^7$, —C(O)NR$^6$R$^7$, —(CR$^{10}$R$^{11}$)$_t$NR$^6$R$^7$, —SO$_2$R$^6$, —SO$_2$NR$^6$R$^7$, (C$_1$-C$_6$)alkyl, —(CR$^{10}$R$^{11}$)$_t$(C$_1$-C$_{10}$)heterocyclic, —(CR$^{10}$R$^{11}$)$_t$O(CR$^{10}$R$^{11}$)$_q$OR$^{10}$, and —(CR$^{10}$R$^{11}$)$_t$OR$^{10}$;

each R$^9$ is independently H, (C$_1$-C$_{10}$)alkyl, —(CR$^{10}$R$^{11}$)$_t$(C$_6$-C$_{10}$)aryl, or —(CR$^1$R$^{11}$)$_t$(C$_1$-C$_{10}$)heterocyclic;

each R$^{10}$ and R$^{11}$ is independently H or (C$_1$-C$_6$)alkyl;

each j is independently 0, 1 or 2;

each t is independently 0, 1, 2, 3, 4, 5 or 6; and each q is independently 2, 3, 4, 5, or 6;

which comprises treating a compound of the formula 12A

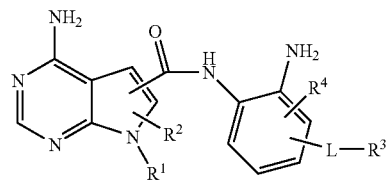

wherein L, R$^1$, R$^2$, and R$^3$ have the same meaning as set forth above for formula 1D, under acidic conditions.

33. The process of claim 32, wherein the compound of formula 12A is treated with acetic acid to prepare the compound of formula 1D.

34. The process of claim 32, wherein the compound of formula 12A is prepared by reacting a compound of formula 11
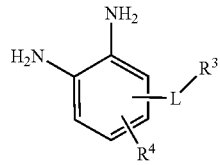
11
wherein L, $R^3$, and $R^4$ have the same meanings as set forth for formula 12A with a compound of formula 7A
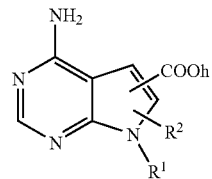
7A
wherein $R^1$ and $R^2$ have the same meanings as set forth for formula 12A.
* * * * *